US010512455B2

(12) United States Patent
Bagaoisan et al.

(10) Patent No.: US 10,512,455 B2
(45) **Date of Patent: *Dec. 24, 2019**

(54) APPARATUS AND METHODS FOR SEALING A VASCULAR PUNCTURE

(71) Applicant: Access Closure, Inc., Santa Clara, CA (US)

(72) Inventors: Celso J Bagaoisan, Union City, CA (US); Sieu Duong, Campbell, CA (US); Fred H. Co, Santa Clara, CA (US); Juan Domingo, Lathrop, CA (US)

(73) Assignee: Access Closure, Inc., Santa Clara, CA (US)

( * ) Notice: Subject to any disclaimer, the term of this patent is extended or adjusted under 35 U.S.C. 154(b) by 445 days.

This patent is subject to a terminal disclaimer.

(21) Appl. No.: 15/154,063

(22) Filed: May 13, 2016

(65) Prior Publication Data

US 2016/0324511 A1 Nov. 10, 2016

Related U.S. Application Data

(60) Division of application No. 13/252,061, filed on Oct. 3, 2011, now Pat. No. 9,364,206, which is a (Continued)

(51) Int. Cl.
*A61B 17/00* (2006.01)

(52) U.S. Cl.
CPC .................... *A61B 17/0057* (2013.01); *A61B 2017/00557* (2013.01); *A61B 2017/00575* (2013.01);

(Continued)

(58) Field of Classification Search
CPC ...... A61B 17/0057; A61B 2017/00575; A61B 2017/00641; A61B 2017/0065; A61B 19/30; A61B 2019/303; A61B 2019/304
See application file for complete search history.

(56) References Cited

U.S. PATENT DOCUMENTS 2,115,492 A 4/1938 Kober
2,365,039 A 12/1944 Andresen (Continued)

FOREIGN PATENT DOCUMENTS

EP 0476178 A1 3/1992
EP 0482350 A2 4/1992

(Continued)

OTHER PUBLICATIONS

St. Jude Medical, Angio-Seal Evolution Vascular Closure Device, Instructions for Use, 2008. 12 pages.

(Continued)

*Primary Examiner* — Dianne Dornbusch
(74) *Attorney, Agent, or Firm* — McDonnell Boehnen Hulbert & Berghoff LLP

(57) ABSTRACT

Apparatus and methods for sealing a puncture through tissue includes an introducer sheath sized for introduction into a puncture, cartridge sized for insertion into the introducer carrying a sealant, and a locking element for coupling the introducer sheath to the cartridge. When the cartridge is advanced into the introducer sheath, the locking element couples the introducer sheath to the cartridge such that subsequent retraction of the cartridge causes the introducer sheath to retract, thereby deploying the sealant from the cartridge within the puncture beyond the introducer sheath.

11 Claims, 14 Drawing Sheets

140 23 124' 28 254 250 120' 127' 122' 123' 20 26 22 29 254a 254b 256 252

Related U.S. Application Data continuation-in-part of application No. 12/098,380, filed on Apr. 4, 2008, now Pat. No. 8,029,533.

(52) U.S. Cl.
CPC ............... *A61B 2017/00601* (2013.01); *A61B 2017/00619* (2013.01); *A61B 2017/00623* (2013.01); *A61B 2017/00654* (2013.01); *A61B 2017/00898* (2013.01)

(56) References Cited

U.S. PATENT DOCUMENTS 3,765,419 A 10/1973 Usher
4,002,173 A 1/1977 Manning et al.
4,260,077 A 4/1981 Schroeder
4,327,709 A 5/1982 Hanson et al.
4,362,150 A 12/1982 Lombardi, Jr. et al.
4,472,542 A 9/1984 Nambu
4,540,404 A 9/1985 Wolvek
4,655,211 A 4/1987 Sakamoto et al.
4,664,857 A 5/1987 Nambu
4,734,097 A 3/1988 Tanabe et al.
4,738,658 A * 4/1988 Magro .................. A61M 25/00 604/158
4,801,434 A 1/1989 Kido et al.
4,838,280 A 6/1989 Haaga
4,838,864 A 6/1989 Peterson
4,852,568 A * 8/1989 Kensey .............. A61B 17/0057 606/213
4,890,612 A * 1/1990 Kensey .............. A61B 17/0057 606/213
5,053,046 A * 10/1991 Janese ................ A61B 17/0057 604/506
5,061,274 A 10/1991 Kensey
5,087,246 A 2/1992 Smith
5,104,375 A 4/1992 Wolf et al.
5,104,389 A 4/1992 Deem et al.
5,108,421 A 4/1992 Fowler
5,192,300 A 3/1993 Fowler
5,192,302 A 3/1993 Kensey et al.
5,221,259 A 6/1993 Weldon et al.
5,222,974 A * 6/1993 Kensey .............. A61B 17/0057 604/15
5,258,042 A 11/1993 Mehta
5,259,835 A 11/1993 Clark et al.
5,275,616 A 1/1994 Fowler et al.
5,282,827 A * 2/1994 Kensey .............. A61B 17/0057 128/887
5,290,310 A 3/1994 Makower et al.
5,292,332 A 3/1994 Lee
5,306,254 A 4/1994 Nash et al.
5,320,639 A 6/1994 Rudnick
5,324,306 A 6/1994 Makower et al.
5,334,216 A 8/1994 Vidal et al.
5,370,660 A 12/1994 Weinstein et al.
5,383,896 A 1/1995 Gershony et al.
RE34,866 E * 2/1995 Kensey .............. A61B 17/0057 606/213
5,391,183 A * 2/1995 Janzen ............... A61B 17/0057 604/15
5,409,703 A 4/1995 McAnalley et al.
5,413,571 A 5/1995 Katsaros et al.
5,419,765 A 5/1995 Weldon et al.
5,431,639 A 7/1995 Shaw
5,437,292 A 8/1995 Kipshidze et al.
5,437,631 A * 8/1995 Janzen ............... A61B 17/0057 128/898
5,441,517 A 8/1995 Kensey et al.
5,443,481 A 8/1995 Lee
5,464,396 A 11/1995 Barta et al.
5,486,195 A 1/1996 Myers et al.
5,489,278 A 2/1996 Abrahamson
5,514,158 A 5/1996 Kanesaka
5,529,577 A 6/1996 Hammerslag
5,550,187 A 8/1996 Rhee et al.
5,571,181 A 11/1996 Li
5,580,923 A 12/1996 Yeung et al.
5,584,815 A 12/1996 Pawelka et al.
5,591,204 A 1/1997 Janzen et al.
5,591,205 A 1/1997 Fowler
5,601,602 A 2/1997 Fowler
5,626,601 A 5/1997 Gershony et al.
5,637,086 A 6/1997 Ferguson et al.
5,643,464 A 7/1997 Rhee et al.
5,649,959 A * 7/1997 Hannam ............ A61B 17/0057 604/181
5,660,849 A 8/1997 Polson et al.
5,681,279 A * 10/1997 Roper ...................... A61D 7/00 604/57
5,700,477 A 12/1997 Rosenthal et al.
5,707,393 A * 1/1998 Kensey ............. A61B 17/0057 128/887
5,716,375 A 2/1998 Fowler
5,718,916 A 2/1998 Scherr
5,725,498 A 3/1998 Janzen et al.
5,725,551 A 3/1998 Myers et al.
5,728,122 A 3/1998 Leschinsky et al.
5,728,132 A 3/1998 Van Tassel et al.
5,731,368 A 3/1998 Stanley et al.
5,741,223 A 4/1998 Janzen et al.
5,744,153 A 4/1998 Yewey et al.
5,752,974 A 5/1998 Rhee et al.
5,759,193 A 6/1998 Burbank et al.
5,780,044 A 7/1998 Yewey et al.
5,782,860 A 7/1998 Epstein et al.
5,785,679 A 7/1998 Abolfathi et al.
5,795,331 A 8/1998 Cragg et al.
5,814,016 A 9/1998 Valley et al.
5,830,130 A 11/1998 Janzen et al.
5,836,970 A 11/1998 Pandit
5,843,124 A 12/1998 Hammerslag
5,868,778 A 2/1999 Gershony et al.
5,916,236 A 6/1999 Muijs Van De Moer et al.
5,922,009 A 7/1999 Epstein et al.
5,928,266 A 7/1999 Kontos
5,941,847 A 8/1999 Huber et al.
5,948,429 A 9/1999 Bell et al.
5,948,829 A 9/1999 Wallajapet et al.
5,951,583 A 9/1999 Jensen et al.
5,951,589 A 9/1999 Epstein et al.
5,957,952 A 9/1999 Gershony et al.
5,972,375 A 10/1999 Truter et al.
5,973,014 A 10/1999 Funk et al.
6,007,563 A * 12/1999 Nash .................. A61B 17/0057 606/213
6,017,359 A 1/2000 Gershony et al.
6,022,361 A 2/2000 Epstein et al.
6,027,471 A 2/2000 Fallon et al.
6,045,570 A 4/2000 Epstein et al.
6,048,358 A 4/2000 Barak
6,051,248 A 4/2000 Sawhney et al.
6,056,768 A 5/2000 Cates et al.
6,056,769 A 5/2000 Epstein et al.
6,063,061 A 5/2000 Wallace et al.
6,063,085 A * 5/2000 Tay .................... A61B 17/0057 606/50
6,083,522 A 7/2000 Chu et al.
6,086,607 A * 7/2000 Cragg ................ A61B 17/0057 604/265
6,090,130 A * 7/2000 Nash .................. A61B 17/0057 604/168.01
6,113,611 A * 9/2000 Allen ................... A61B 17/064 606/151
6,117,145 A 9/2000 Wood et al.
6,152,943 A 11/2000 Sawhney
6,162,192 A * 12/2000 Cragg ................ A61B 17/0057 604/15
6,162,240 A * 12/2000 Cates ................. A61B 17/0057 606/213
6,162,241 A 12/2000 Coury et al.
6,165,201 A 12/2000 Sawhney
6,179,862 B1 1/2001 Sawhney

(56) References Cited

U.S. PATENT DOCUMENTS 6,179,863 B1 * 1/2001 Kensey .............. A61B 17/0057 606/215
6,223,936 B1 5/2001 Jeanbourquin
6,238,412 B1 5/2001 Dubrul et al.
6,271,278 B1 8/2001 Park et al.
6,287,323 B1 9/2001 Hammerslag
6,296,658 B1 10/2001 Gershony et al.
6,299,597 B1 10/2001 Buscemi et al.
6,302,898 B1 10/2001 Edwards et al.
6,315,753 B1 * 11/2001 Cragg ................ A61B 17/0057 604/15
6,325,789 B1 * 12/2001 Janzen ............... A61B 17/0057 604/15
6,350,274 B1 2/2002 Li
6,368,300 B1 4/2002 Fallon et al.
6,371,975 B2 4/2002 Cruise et al.
6,379,373 B1 4/2002 Sawhney et al.
6,458,147 B1 10/2002 Cruise et al.
6,464,712 B1 10/2002 Epstein et al.
6,475,177 B1 * 11/2002 Suzuki ............... A61B 17/0057 604/11
6,514,534 B1 2/2003 Sawhney
6,540,735 B1 * 4/2003 Ashby ................ A61B 17/0057 604/15
6,562,059 B2 5/2003 Edwards et al.
6,566,406 B1 5/2003 Pathak et al.
6,569,185 B2 5/2003 Ungs
6,605,294 B2 8/2003 Sawhney
6,608,117 B1 8/2003 Gvozdic
6,610,026 B2 8/2003 Cragg et al.
6,613,070 B2 9/2003 Redmond et al.
6,626,861 B1 9/2003 Hart et al.
6,626,918 B1 9/2003 Ginn et al.
6,635,068 B1 10/2003 Dubrul et al.
6,689,148 B2 2/2004 Sawhney et al.
6,699,261 B1 3/2004 Cates et al.
6,703,047 B2 3/2004 Sawhney et al.
6,774,151 B2 8/2004 Malmgren et al.
6,818,008 B1 11/2004 Cates et al.
6,818,018 B1 11/2004 Sawhney
6,860,895 B1 * 3/2005 Akerfeldt ........... A61B 17/0057 606/139
6,863,924 B2 3/2005 Ranganathan et al.
6,887,974 B2 5/2005 Pathak
6,890,342 B2 5/2005 Zhu et al.
6,890,343 B2 5/2005 Ginn et al.
6,960,617 B2 11/2005 Omidian et al.
6,994,686 B2 2/2006 Cruise et al.
7,009,034 B2 3/2006 Pathak
7,118,578 B2 10/2006 West et al.
7,316,704 B2 1/2008 Bagaoisan et al.
7,331,979 B2 2/2008 Khosravi et al.
7,335,220 B2 * 2/2008 Khosravi ......... A61B 17/00491 606/213
7,553,319 B2 6/2009 Bagaoisan et al.
7,572,274 B2 8/2009 Yassinzadeh
7,611,479 B2 11/2009 Cragg et al.
7,618,438 B2 * 11/2009 White ................ A61B 17/0057 606/232
7,621,936 B2 11/2009 Cragg et al.
7,662,161 B2 * 2/2010 Briganti ............. A61B 17/0057 606/151
7,790,192 B2 9/2010 Khosravi
7,806,856 B2 10/2010 Bagaoisan et al.
7,850,710 B2 12/2010 Huss
7,955,353 B1 6/2011 Ashby et al.
7,988,706 B2 8/2011 Forsberg et al.
7,993,367 B2 8/2011 Bagaoisan et al.
8,002,742 B2 8/2011 Pai et al.
8,262,693 B2 9/2012 Pai et al.
8,568,445 B2 10/2013 Pipenhagen et al.
8,795,709 B2 8/2014 Sawhney et al.
8,870,917 B2 10/2014 Walters
9,289,195 B2 3/2016 Bagaoisan et al.
9,668,719 B2 6/2017 Tegels et al.
9,895,144 B2 2/2018 Tegels et al.
2001/0031948 A1 10/2001 Cruise et al.
2001/0046518 A1 11/2001 Sawhney
2001/0047187 A1 11/2001 Milo et al.
2001/0051813 A1 12/2001 Hnojewyj
2002/0015724 A1 2/2002 Yang et al.
2002/0062104 A1 5/2002 Ashby et al.
2002/0072767 A1 6/2002 Zhu et al.
2002/0106409 A1 8/2002 Sawhney et al.
2002/0111392 A1 8/2002 Cruise
2002/0111651 A1 8/2002 Ungs
2002/0188319 A1 * 12/2002 Morris ............... A61B 17/0057 606/213
2002/0193808 A1 12/2002 Belef et al.
2003/0008831 A1 1/2003 Yang et al.
2003/0012734 A1 1/2003 Pathak et al.
2003/0051735 A1 3/2003 Pavcnik et al.
2003/0088269 A1 5/2003 Ashby
2003/0088271 A1 5/2003 Cragg et al.
2003/0109899 A1 6/2003 Fisher et al.
2003/0135234 A1 7/2003 Fisher et al.
2003/0135235 A1 7/2003 Fisher et al.
2003/0135236 A1 7/2003 Fisher et al.
2003/0135237 A1 * 7/2003 Cragg ................ A61B 17/0057 606/213
2003/0139770 A1 7/2003 Fisher et al.
2003/0139771 A1 7/2003 Fisher et al.
2003/0139772 A1 7/2003 Fisher et al.
2003/0139773 A1 7/2003 Fisher et al.
2003/0233120 A1 12/2003 Akerfeldt et al.
2004/0010287 A1 1/2004 Bonutti
2004/0122350 A1 6/2004 Zhong et al.
2004/0143290 A1 7/2004 Brightbill
2004/0147016 A1 7/2004 Rowley et al.
2004/0176798 A1 9/2004 Epstein et al.
2004/0236262 A1 11/2004 McIntosh et al.
2004/0249342 A1 12/2004 Khosravi et al.
2004/0267193 A1 12/2004 Bagaoisan et al.
2004/0267307 A1 12/2004 Bagaoisan et al.
2004/0267308 A1 * 12/2004 Bagaoisan ......... A61B 17/0057 606/213
2005/0085773 A1 4/2005 Forsberg
2005/0085851 A1 * 4/2005 Fiehler ............... A61B 17/0057 606/213
2005/0085852 A1 * 4/2005 Ditter ................. A61B 17/0057 606/213
2005/0085855 A1 * 4/2005 Forsberg ............ A61B 17/0057 606/213
2005/0267522 A1 12/2005 Yassinzadeh et al.
2005/0277980 A1 12/2005 Yassinzadeh
2006/0034930 A1 * 2/2006 Khosravi ......... A61B 17/00491 424/484
2006/0099238 A1 5/2006 Khosravi et al.
2006/0100664 A1 5/2006 Pai et al.
2006/0161188 A1 7/2006 Kennedy et al.
2006/0229673 A1 * 10/2006 Forsberg ............ A61B 17/0057 606/232
2006/0229674 A1 * 10/2006 Forsberg ............ A61B 17/0057 606/232
2006/0241579 A1 * 10/2006 Kawaura ............ A61B 17/0057 606/39
2006/0253037 A1 11/2006 Ginn et al.
2006/0253072 A1 11/2006 Pai et al.
2006/0265007 A1 * 11/2006 White ................ A61B 17/0057 606/232
2007/0060950 A1 3/2007 Khosravi et al.
2007/0088362 A1 4/2007 Bonutti et al.
2007/0231366 A1 10/2007 Sawhney et al.
2007/0255314 A1 * 11/2007 Forsberg ............ A61B 17/0057 606/213
2008/0009794 A1 1/2008 Bagaoisan et al.
2008/0082122 A1 4/2008 Khosravi et al.
2008/0221615 A1 9/2008 Ginn et al.
2008/0243182 A1 10/2008 Bates et al.
2008/0269800 A1 10/2008 Spurchise et al.
2009/0088793 A1 4/2009 Bagaoisan et al.
2009/0318955 A1 12/2009 Dave et al.

(56) References Cited

U.S. PATENT DOCUMENTS

| | | | |
|---|---|---|---|
| 2010/0211000 | A1 | 8/2010 | Killion et al. |
| 2013/0190813 | A1 | 7/2013 | Tegels et al. |
| 2014/0135826 | A1 | 5/2014 | Tegels et al. |
| 2014/0180334 | A1 | 6/2014 | Bagaoisan et al. |

FOREIGN PATENT DOCUMENTS

| | | | |
|---|---|---|---|
| EP | 0716833 | A2 | 6/1996 |
| EP | 2811912 | B1 | 6/2017 |
| WO | 9222252 | A1 | 12/1992 |
| WO | 9413210 | A1 | 6/1994 |
| WO | 9428798 | A1 | 12/1994 |
| WO | 9922646 | A1 | 5/1999 |
| WO | 0014155 | A1 | 3/2000 |
| WO | 0019912 | A1 | 4/2000 |
| WO | 03004749 | A1 | 1/2003 |
| WO | 03009764 | A1 | 2/2003 |
| WO | 03087254 | A2 | 10/2003 |
| WO | 03094749 | A1 | 11/2003 |
| WO | 2006115904 | A2 | 11/2006 |
| WO | 2008036634 | A1 | 3/2008 |

OTHER PUBLICATIONS

Office Actions and Responses for related U.S. Appl. No. 11/864,835, filed Sep. 28, 2007; First named Inventor: Celso J. Bagaoisan; dated Mar. 1, 2010-Feb. 4, 2011; 46 pages.

PCT International Search Report and Written Opinion for International Application No. PCT/US2008/077406 (ACI-028 WO), Applicant: AccessCiosure, Inc., Forms PCT/ISA/220, PCT/ISA/210, and PCT/ISA/237, dated Dec. 22, 2008, 11 pages.

* cited by examiner 252
120'
254
250
28
256
124'
20
23
90
140
92
96
94
146

123'
122'
252
250
250
20
259
258
127
254
256
90
120'
92
96
2
130
94
146

350
320
28
352
356
20
353
354
92
96
140
94
146

323
140
327
352
322

28
350
356
20
353
320
354
92
96
324
2
130
94
146

APPARATUS AND METHODS FOR SEALING A VASCULAR PUNCTURE

RELATED APPLICATION DATA

This application is a divisional of co-pending application Ser. No. 13/252,061, filed Oct. 3, 2011, which is a continuation-in-part of application Ser. No. 12/098,380, filed Apr. 4, 2008, and now U.S. Pat. No. 8,029,533, the entire disclosure of both is expressly incorporated by reference herein.

FIELD OF THE INVENTION

The present invention relates generally to apparatus and methods for sealing punctures in a body, and more particularly, to apparatus and methods for sealing a vascular puncture extending through tissue into a blood vessel, and to apparatus and methods for delivering a plug, sealant, and/or other material into a percutaneous puncture extending from a patient's skin to a blood vessel or other body lumen, e.g., to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 to Fowler discloses a plug that may be delivered into a puncture through tissue. U.S. Pat. Nos. 5,192,302 and 5,222,974 issued to Kensey et al. describe a bioabsorbable collagen plug that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism.

U.S. Pat. No. 6,605,294 describes rods, plugs, and crushed or irregularly shaped pieces of substantially dehydrated hydrogel that may be introduced into a lumen or void in a patient's body, e.g., to seal or plug a biopsy needle track, reinforce weak tissue, or deliver a therapeutic compound. In one embodiment, a plug of dehydrated hydrogel may be deployed into the site of an arteriotomy and allowed to hydrate in the presence of the tissue fluids and blood, to fill the tract of the catheter sheath and prevent further bleeding. By swelling to equilibrium hydration, the plug may lock itself firmly in place and thus reduce the risk of formation of a large hematoma at the site of the puncture.

U.S. Pat. No. 6,703,047 discloses dehydrated hydrogel precursor-based, tissue adherent compositions. The hydrogels may be used, for example, for sealing fluid leaks from tissue, as adherent drug delivery depots, and as means for augmenting and/or supporting tissue. The hydrogels may be administered directly to an open wound site or may be dispensed, e.g., using a non-adhesive backing material, an absorbable backing material, a syringe applicator, a powder atomization or aerosolization system, or a needle-less injector.

SUMMARY OF THE INVENTION

The present invention is directed to apparatus and methods for sealing a puncture in a body, and, more particularly, to apparatus and methods for providing temporary or permanent hemostasis within a vascular puncture extending into a blood vessel, and/or to apparatus and methods for delivering a sealant and/or other material into a percutaneous puncture extending from a patient's skin to a blood vessel or other body lumen.

In accordance with one embodiment, an apparatus is provided for sealing a puncture extending through tissue that includes an introducer sheath including a distal end sized to be introduced in a puncture, and a cartridge or other tubular member including a proximal end, a distal end sized for insertion into the introducer sheath, a lumen extending between the tubular member proximal and distal ends, and a distal opening in communication with the lumen. The apparatus includes a locking element for engaging a portion of the introducer sheath to the tubular member to couple subsequent movement of the introducer sheath to the tubular member, e.g., once the tubular member distal end enters the introducer sheath. A sealant may be disposed within the tubular member, e.g., within the lumen adjacent the distal opening, and a pusher member may be disposed within the lumen for deploying the sealant from the tubular member, e.g., out the distal opening into a puncture or other passage through tissue.

Optionally, the introducer sheath may include an abutment or other feature on its proximal end for engaging the locking element when the tubular member is advanced into the introducer sheath. Alternatively, the introducer sheath may include one or more seals on the proximal end and/or a hub on the proximal end that engage with the locking element when the tubular member is advanced into the introducer sheath.

In one embodiment, the locking element may include a coil carried by the tubular member. One or more windings of the coil may engage the introducer sheath, e.g., the abutment, seal(s), hub, or other features on the introducer sheath, when the tubular member is advanced into the introducer sheath, coupling subsequent movement of the introducer sheath to the tubular member. Such coupling may prevent the sealant from being prematurely deployed from the tubular member, e.g., within the introducer sheath, by coupling retraction of the introducer sheath and tubular member, as described further elsewhere herein.

In another embodiment, the locking element may include one or more prongs, fingers, or other detents that engage the abutment, seal(s), hub, or other features on the introducer sheath. The prongs may be compressed by the introducer sheath to a compressed position, but may expand to an expanded position when advanced distally beyond the abutment, seal(s), hub, or other features. Subsequent proximal movement of the tubular member causes the prongs to engage the features on the introducer sheath, thereby retracting the introducer sheath together with the tubular member, i.e., limiting subsequent proximal movement of the tubular member separate from the introducer sheath. Optionally, the prongs may be provided on a sleeve disposed over the tubular member or between the tubular member and the introducer sheath. For example, the sleeve may be free to "float" on a catheter or other elongate positioning member received through the tubular member and introducer sheath. At least a portion of the sleeve may have a diameter larger than a lumen of the introducer sheath, such that the distance the prongs are inserted into the introducer sheath is limited when the sleeve contacts the proximal end of the introducer sheath.

In another embodiment, the locking element may include an assembly with an expandable tube coupled to a locking hub through which the tubular member may be received. The assembly may be received in the lumen of the introducer sheath, e.g., such that the expandable tube is inserted at least partially into the hub or proximal end of the introducer sheath, e.g., distally beyond the abutment, seal(s), or other feature(s). Subsequently, when the tubular member is advanced through the expandable tube, the tube is directed to an expanded position, such that subsequent proximal retraction of the tubular member causes the expandable tube to engage the feature(s) on the introducer sheath. Thus, the introducer sheath becomes coupled to the tubular member, thereby limiting subsequent movement of the tubular member separate from the introducer sheath.

The diameter of the locking hub may be greater than that of the lumen of the introducer sheath, such that the locking hub limits advancing the expandable tube into the introducer sheath, e.g., when the locking hub contacts the proximal end of the introducer sheath. Optionally, the locking hub may receive one or more barbs, tabs, or other detents on the tubular member, e.g., on a handle portion of the tubular member for coupling the locking hub and expandable tube to the tubular member. When the locking hub receives the detent(s), the locking hub may prevent subsequent withdrawal of the detent(s), thereby coupling the introducer sheath to the tubular member via the locking element and/or preventing the sealant from being deployed from the tubular member into the introducer sheath.

In still another embodiment, the locking element may include a bellows or compressible sleeve, e.g., that may be disposed around the cartridge. When the cartridge is advanced into the introducer sheath, the bellows may at least partially enter the introducer sheath and become compressed and/or expanded to engage one or more features within the introducer sheath to couple subsequent movement of the introducer sheath to the cartridge. Optionally, the bellows may include a handle or other safety feature, e.g., on a proximal end of the bellows, that may be pulled to extend and/or collapse the bellows if it is desired to disengage the introducer sheath from the cartridge.

The sealant may include a variety of materials, such as dried or freeze-dried hydrogel material, which may hydrate and/or otherwise expand when exposed to an aqueous physiological environment. In exemplary embodiments, the sealant may include a plug or core, e.g., of freeze-dried hydrogel, and a coating on at least a portion of the core, e.g., including one or more precursors, which may remain in an unreactive state until exposed to an aqueous physiological environment, whereupon the precursor(s) may react, e.g., to form an adherent coating on the core. Optionally, an activating agent, e.g., a pH adjusting material, may be disposed on at least a portion of the core, the activating agent facilitating or initiating reaction of the first and second precursors when exposed to an aqueous physiological environment.

In accordance with another embodiment, an apparatus is provided for sealing a puncture extending through tissue and communicating with a body lumen that includes an introducer sheath including a proximal end, a distal end sized for introduction into a puncture or other passage through tissue, and a lumen extending between the proximal and distal ends, and a cartridge or other tubular member including a proximal end, a distal end sized for insertion into the introducer sheath, a lumen extending between the proximal and distal ends, and a locking element for coupling the introducer sheath to the tubular member. A sealant may be disposed within the lumen of the tubular member, e.g., adjacent the distal end, and a pusher member may be disposed within the tubular member lumen for deploying the sealant from the tubular member.

The pusher member and sealant may include a lumen extending therethrough, and the apparatus may include an elongate positioning member including a proximal end slidable through the sealant lumen and the pusher member lumen. The positioning member may include an expandable positioning element on a distal end thereof for preventing the positioning element from being removed from the body lumen into the puncture after being deployed within the body lumen and/or for sealing the body lumen from the puncture.

In accordance with still another embodiment, a method is provided for sealing a puncture extending through tissue to a body lumen. A positioning member may be introduced into the puncture through an introducer sheath until a positioning element thereon is exposed within the body lumen, the positioning element may be expanded, and the positioning member may be retracted until the expanded positioning element contacts a wall of the body lumen. A cartridge or other tubular member carrying a sealant is introduced through the introducer sheath and over the positioning member until the sealant is disposed proximate the positioning element.

When the tubular member is introduced into the introducer sheath, the introducer sheath is coupled to the tubular member. The tubular member is then retracted relative to the sealant to expose the sealant within the puncture, e.g., adjacent the body lumen. Because the introducer sheath is coupled to the tubular member, retraction of the tubular member automatically withdraws the introducer sheath from the puncture, thereby exposing the sealant within the puncture beyond the introducer sheath. Optionally, the sealant may be cinched or otherwise compressed within the puncture, e.g., using a pusher member also carried within the tubular member.

When the sealant is exposed to bodily fluid when the tubular member is retracted, the sealant may hydrate and/or expand to enhance sealing the puncture. The positioning element may be collapsed and the positioning member may be withdrawn from the body lumen and puncture, e.g., while the pusher member prevents substantial migration of the sealant. Finally, the pusher member may be removed, leaving the sealant within the puncture to achieve hemostasis.

Other aspects and features of the present invention will become apparent from consideration of the following description taken in conjunction with the accompanying drawings.

DETAILED DESCRIPTION OF THE EXEMPLARY EMBODIMENTS

Figure 1A:
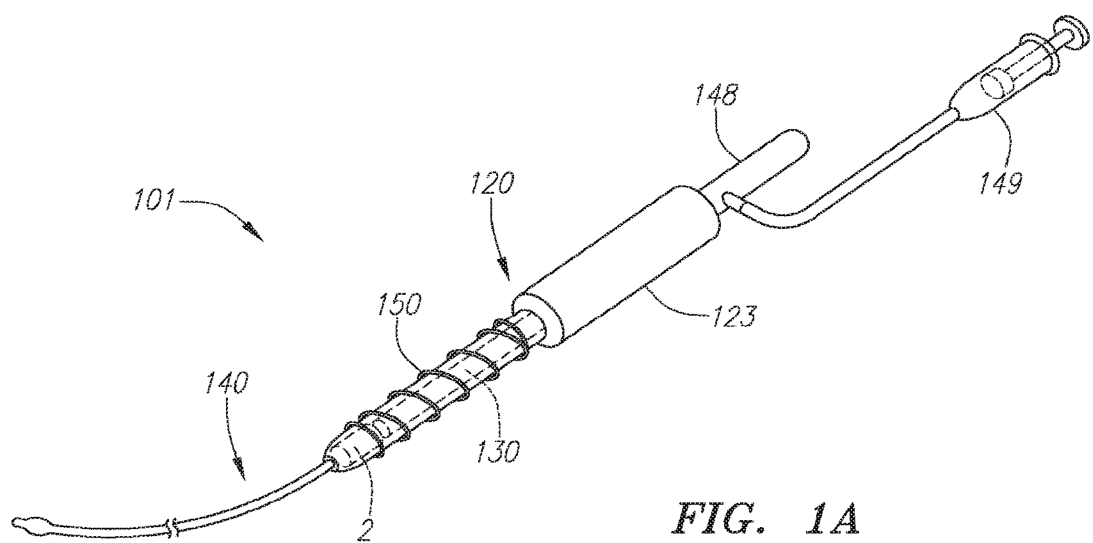
FIG. 1A is a perspective view of an exemplary embodiment of an apparatus for delivering a sealant into a puncture through tissue, including a cartridge carrying the sealant and a positioning member.

Turning to the drawings, FIGS. 1A-2B show an exemplary embodiment of an apparatus 101 for sealing a puncture through tissue. Generally, as shown in FIG. 1A, the apparatus 101 includes a cartridge or other tubular member 120, a sealant 2 carried by the cartridge 120, a plunger, tamping member, or other pusher member 130 also carried by the cartridge 120, a positioning member 140, and a locking element 150. As shown in FIG. 1B, the apparatus 101 may be part of a system 10, e.g., which may also include a delivery, access, procedure, introducer, or other sheath 20. Optionally, the system 10 may include one or more other components, e.g., a needle, guidewire, and/or other instrument for creating a puncture (not shown), and/or a source of additional sealing compound (also not shown).

Figure 1B:
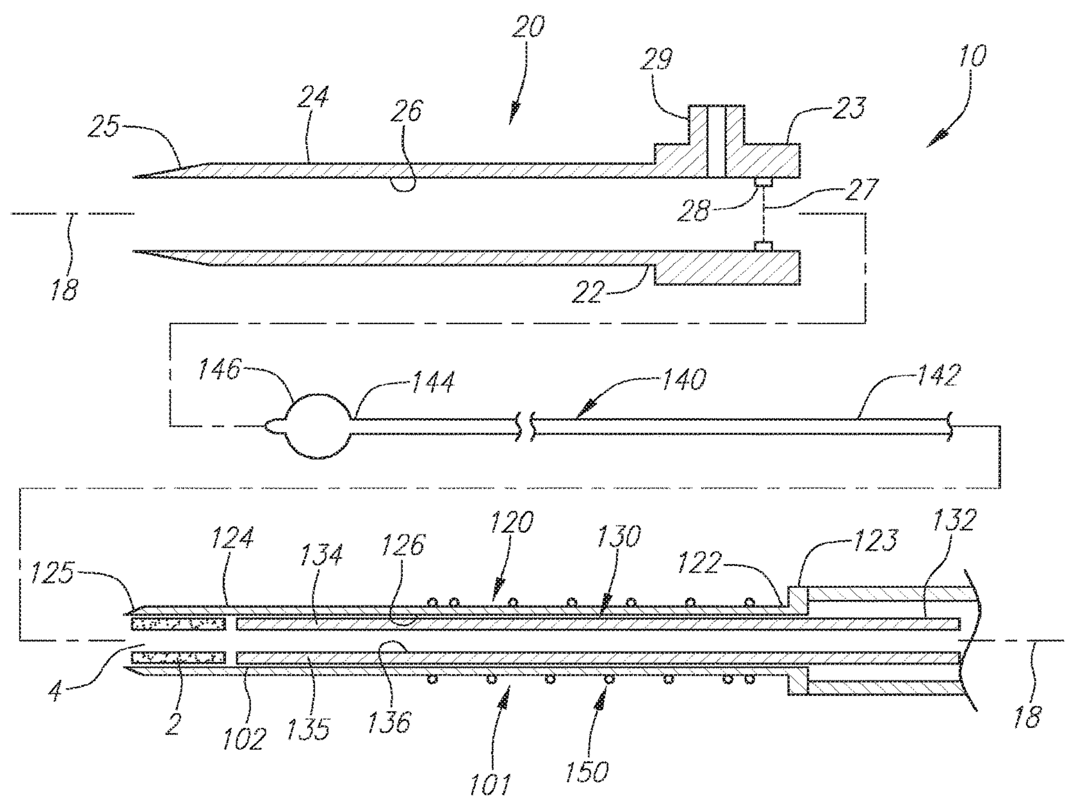
FIG. 1B is an exploded side view of a system for delivering a sealant into a puncture through tissue, including the apparatus of FIG. 1A and an introducer sheath.

As best seen in FIG. 1B, the introducer sheath 20 generally includes a proximal end 22, a distal end 24 sized for insertion into a puncture through tissue, and a lumen 26 extending between the proximal and distal ends 22, 24. The introducer sheath 20 may be formed from a substantially rigid, semi-rigid, and/or flexible tubular body including a hub 23 on the proximal end 22. The introducer sheath 20 may have sufficient length to extend from a patient's skin through any intervening tissue into a blood vessel or other body lumen, e.g., having a length between about ten centimeters and twenty centimeters (10-20 cm), and may have an outer diameter between about 1.6 millimeters and 4 millimeters (1.6-4 mm). The distal end 24 may be tapered and/or may include a substantially atraumatic distal tip 25 for facilitating advancement through a puncture.

The introducer sheath 20 may be formed using known materials and/or methods, e.g., plastic with the tubular body and hub 23 substantially permanently connected together, e.g., using an interference fit, one or more mating connectors (not shown), bonding with adhesive, sonic welding, and the like. The hub 23 generally includes one or more seals (not shown) adjacent an opening 27, which may prevent flow of blood or other fluids out of the hub 23 from the lumen 26, yet accommodate insertion of one or more instruments into the lumen 26, such as the cartridge 120. Optionally, as shown, the hub 23 may include a side port 29 communicating with the lumen 26, e.g., for coupling a source of saline or other fluid (not shown) to the hub 23.

The hub 23 also includes one or more abutments 28 therein, e.g., adjacent opening 27. For example, the hub 23 may include one or more annular ridges, tabs, grooves, lips and the like, which may provide abutment(s) 28 for interlocking or otherwise engaging with the locking element 150, as described elsewhere herein. Alternatively, the seal(s) within the hub may provide sufficient abutment for engaging with the locking element 150, thereby obviating the need for separate ridges or grooves.

Figure 2A:
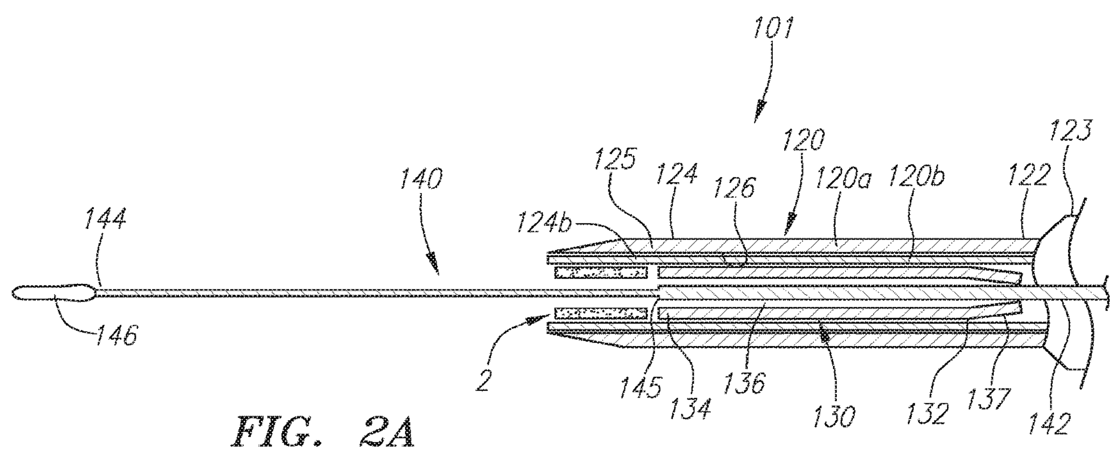
FIGS. 2A and 2B are cross-sectional views of the apparatus of FIGS. 1A and 1B, with the cartridge in proximal and distal positions, respectively.
Figure 2B:
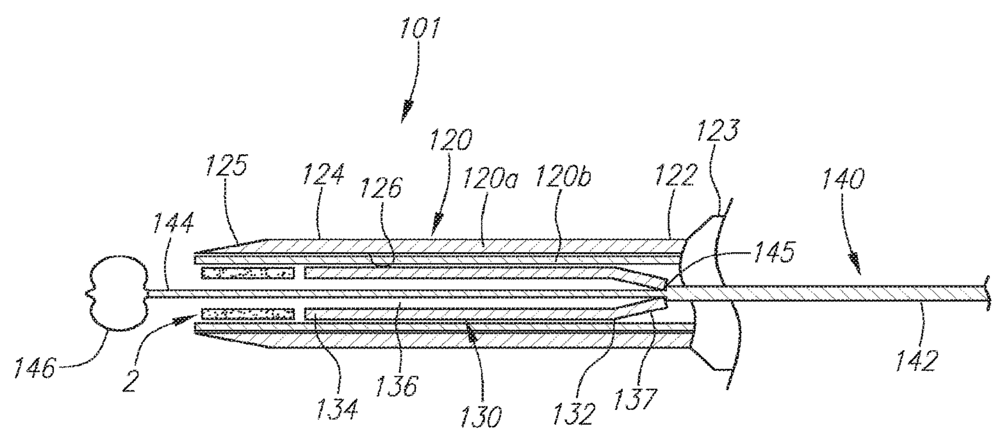

With additional reference to FIGS. 2A and 2B, the cartridge 120 is generally an elongate tubular body including a proximal end 122, a distal end 124 sized for introduction into the lumen 26 of the introducer sheath 20, and a lumen 126 extending between the proximal and distal ends 122, 124. The cartridge 120 may be substantially rigid, semi-rigid, or flexible, e.g., such that the cartridge 120 may be advanced through the introducer sheath 20 or otherwise into a puncture through tissue. The cartridge 120 may also include a tapered distal tip 125 and/or an enlarged handle or hub 123 on the proximal end 122, e.g., as shown in FIG. 1A.

Additionally, as shown in FIGS. 1A and 1B, the cartridge 120 may include a locking element 150 for engaging the abutment(s) 28 in the lumen 26 of the introducer sheath 20. The locking element 150 couples the introducer sheath 20 to the cartridge 120 during use such that subsequent movement of the cartridge 120, e.g., proximally during retraction, causes the introducer sheath 20 to be pulled or otherwise moved along with the cartridge 20. As described elsewhere herein, this coupling may prevent accidental proximal movement of the cartridge 120 independent of the introducer sheath 20, which may otherwise result in deploying the sealant 2 from the cartridge 120 within the introducer sheath 20, rather than within a puncture itself. Embodiments of the locking element are described in further detail elsewhere herein.

With further reference to FIGS. 2A and 2B, the pusher member 130 may be an elongate tubular body, e.g., a plunger or catheter, including a proximal end 132, a distal end 134 sized for introduction into the lumen 126 of the cartridge 120, and a lumen 136 extending between the proximal and distal ends 132, 134. The pusher member 130 may be sized for being slidably received within the lumen 126 of the cartridge 120, although the pusher member 130 may abut or otherwise interact with the hub 123 of the cartridge 120 such that the pusher member 130 is advanced distally when the cartridge 120 is advanced. The distal end 134 of the pusher member 130 may terminate in a substantially blunt distal tip 135, e.g., to facilitate contacting, pushing, and/or "cinching" the sealant 2 within a puncture, as described further below.

The pusher member 130 may be substantially rigid, semi-rigid, and/or substantially flexible, having sufficient column strength to allow proximal movement of the cartridge 120 relative to the sealant 2 without buckling the pusher member 130 and/or to allow the distal end 134 of the pusher member 130 to be "tamped" down on sealant 2 within a puncture, e.g., by pushing from the proximal end 132, as described elsewhere herein. The pusher member 130 may also include a lumen 136 extending between the proximal and distal ends 132, 134, e.g., to accommodate the positioning member 140, a guidewire (not shown), a flowable sealing compound, and/or fluid.

As shown in FIGS. 2A and 2B, the pusher member 130 may include one or more elements 137 on the proximal end 132, e.g., for interacting with one or more cooperating elements 145 on the positioning member 140, as described elsewhere herein. As shown, the element(s) 137 may simply be a relatively narrow region on the proximal end 132. Alternatively, the element(s) 137 may be a separate collar or sleeve, one or more inwardly oriented detents, and the like (not shown) attached to or otherwise formed on the proximal end 132 of the pusher member 130.

The sealant 2 may be disposed within the lumen 126 of the cartridge 120 proximate to the distal end 124, e.g., immediately adjacent the distal tip 125. The lumen 126 may be sized such that the cartridge and sealant 2 are slidable relative to one another, e.g., to allow the cartridge 120 to be retracted proximally relative to the sealant 2 and/or pusher member 130.

Optionally, as shown in FIGS. 2A and 2B, the cartridge 120 may include an inner tubular member 120*b* disposed between an outer tubular member 120*a* and the pusher member 130. The outer and inner tubular members 120*a*, 120*b* may be coupled together such that both tubular members 120*a*, 120*b* are retracted proximally when the hub 123 is pulled proximally after advancement into a puncture, as described elsewhere herein. The inner tubular member 120*b* may include a split distal end 124*b*, e.g., formed by creating one or more relatively short longitudinal cuts or slots extending proximally from the distal end 124*b*. The split distal end 124*b* may facilitate retraction of the cartridge 120 relative to the sealant 2, e.g., by providing extra flexibility at the distal end 124, which may allow the distal end 124 to separate more easily from the sealant 2, e.g., as the sealant begins to expand upon being exposed to an aqueous environment.

With continued reference to FIGS. 2A and 2B, the positioning member 140 generally is an elongate member including a proximal end 142, a distal end 144, and a positioning or occlusion element 146 on the distal end 144. The positioning element 146 may be an expandable member, such as a balloon, a wire mesh structure, an expandable frame, and the like. The positioning element 146 may be selectively expandable, e.g., using a source of inflation media, a pull wire, and/or other actuator (not shown), operable from the proximal end 142 of the positioning member 140.

For example, as shown in FIG. 1A, the positioning element may be a balloon 146, and the positioning member 140 may be a tubular body including a lumen (not shown) extending between the proximal and distal ends 142, 144 and communicating with an interior of the balloon 146. In this embodiment, the positioning member 140 may include a source of inflation media, e.g., a syringe 149 coupled to a housing 148 on the proximal end 142 of the positioning member 140. Optionally, the positioning member 140 may include an internal pull wire (not shown) that causes the balloon 146 to shorten during expansion and extend during collapse. Exemplary embodiments of positioning members 140 including balloons that may be used are disclosed in co-pending application Ser. No. 10/454,362, filed Jun. 4, 2003, published as US 2004/0249342, Ser. No. 11/112,877, filed Apr. 22, 2005, published as US 2006/0253072, and Ser. No. 11/112,971, filed Apr. 22, 2005, and published international application WO 2006/115904. The entire disclosures of these references are expressly incorporated by reference herein.

Alternatively, the positioning element may be biased to an enlarged condition, but may be compressed to a contracted condition, e.g., by an overlying sleeve or other constraint (not shown). The constraint may be removed to expose the positioning element, allowing the expandable element to automatically expand to the enlarged condition. Additional information on expandable structures that may be provided on the positioning member 140 may be found in U.S. Pat. Nos. 6,238,412, 6,635,068, and 6,890.343, and in co-pending application Ser. No. 10/975,205, filed Oct. 27, 2004. The entire disclosures of these references are expressly incorporated herein by reference.

Returning to FIGS. 1A and 1B, the sealant 2 may include a biocompatible, bioabsorbable, and/or expandable material, such as a freeze-dried hydrogel. The sealant 2 may have a solid or hollow cylindrical shape, a rolled sheet shape, a disk shape, or other shapes or cross-sections, such as elliptical, triangular, square, conical, disk, polygonic shapes. For example, the sealant 2 may be formed from a solid material including a lumen 4 extending between proximal and distal ends thereof. The lumen 4 may be created by rolling a sheet of material around a mandrel, by molding, by boring into or otherwise removing material from an already formed solid material, and the like. The lumen 4 may be dimensioned such that the positioning member 140, a guidewire or other instrument (not shown) may slide or otherwise pass through the sealant 2, as described elsewhere herein.

The sealant 2 may be substantially homogeneous, or may include one or more different materials at one or more locations. For example, in one embodiment, the sealant 2 may include a carrier or core having first and second hydrogel precursors disposed thereon in an unreactive state, which may provide an adherent coating when the sealant 26 is exposed to an aqueous environment. In one embodiment, the sealant 2 may be formed from a biocompatible and/or bioabsorbable hydrogel, e.g., polyethylene glycol ("PEG"), or other synthetic material. For example, the hydrogel may include a lyophilized (i.e., freeze-dried) PEG polymer that includes hydrolytically degradable chemical groups, e.g., including a macroporous polymer network, which may uptake fluid and expand when exposed to an aqueous environment. The magnitude of expansion or swelling (pre to post hydration) may be significant, e.g., between about two and ten times (2×-10×) its lyophilized size based on volume.

In addition or alternatively, the sealant 2 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. Optionally, the sealant 2 may include one or more therapeutic and/or pharmaceutical agents, e.g., to promote healing, prevent infection and/or other adverse medical events, and the like. Such agents may be embedded in the sealant material and/or applied as one or more coatings or layers. Exemplary materials and methods for making and using them are disclosed in U.S. Pat. Nos. 6,152,943, 6,165,201, 6,179,862, 6,514,534, 6,379,373, 6,703,047, and in co-pending application Ser. No. 10/010,715 filed Nov. 9, 2001, Ser. No. 10/068,807 filed Feb. 5, 2002, Ser. No. 10/454,362, filed Jun. 4, 2003, published as US 2004/0249342, Ser. No. 10/982,387, filed Nov. 5, 2004, published as US 2006/0034930, Ser. No. 10/982,384, filed Nov. 5, 2004, published as US 2006/0099238, and Ser. No. 11/465,791, filed Aug. 18, 2006. The disclosures of these references are expressly incorporated by reference herein.

Turning to FIGS. 2A and 2B, the apparatus 101 may be used to position and deliver the sealant 2 within a puncture, e.g., extra-vascularly just above or otherwise adjacent to an arteriotomy in a blood vessel or other body lumen communicating with a puncture, as described further elsewhere herein. In one embodiment, as shown in FIG. 2A, the cartridge 120 (along with the pusher member 130 and sealant 2) may be initially provided on the proximal end 142 of the positioning member 140. For example, the housing 148 (not shown, see FIG. 1A) on the positioning member 140 and the hub 123 on the cartridge 120 may be initially connected to one another, e.g., using one or more releasable detents and the like. The cartridge 120 may be slidable distally along the positioning member 140, e.g., by disconnecting the hub 123 from the housing 148, and then advancing the cartridge 120 until the distal end 124 of the cartridge 120 is disposed adjacent the positioning element 146, as shown in FIG. 2B. For example, the detents may simply separate from one another when the hub 123 is advanced away from the housing 148 with sufficient force. Alternatively, one of the hub 123 and housing 148 may include an actuator or lock that may be activated (not shown) to separate the detents and/or otherwise allow the cartridge 120 to be advanced relative to the positioning member 140.

Optionally, the positioning member 140 and/or pusher member 130 may include one or more elements that engage when the cartridge 120 reaches a predetermined location when advanced along the positioning member 140, e.g., to limit subsequent proximal movement of the pusher member 130 relative to the positioning member 140. For example, as shown in FIGS. 2A and 2B, the positioning member 140 may include a reduced diameter region 145 at a predetermined location, e.g., by providing a larger tube around a smaller inner tube or by machining, etching, or otherwise removing a portion of the tubular body of the positioning member 140 distal to the reduced region 145. The pusher member 130 may include a living hinge, tab, or other element 137 on the proximal end 132 that may pass freely over the reduced region 145, yet may be unable to pass proximally back over the reduced region 145. Alternatively, the positioning member 140 may include a ring, tab, or other raised element (not shown) and the pusher member 130 may include a corresponding element (also not shown) that may allow distal advancement but prevent proximal retraction once the pusher member 130 is advanced a predetermined distance.

The reduced region 145 may be provided at a predetermined location on the positioning member 140, e.g., a predetermined distance from the positioning element 146 that corresponds to a length of the pusher member 130. As the cartridge 120 (and consequently the pusher member 130) is advanced over the positioning member 140, e.g., until the sealant 2 is disposed adjacent the positioning element 146, the element 137 may pass freely over the reduced region 145. Thereafter, the element 137 may prevent the pusher member 130 from being retracted again past the reduced region 145, due to the blunt edge of the element 137 abutting the abrupt transition of the reduced region 145.

Alternatively, the cartridge member 120 and pusher member 130 may be provided initially adjacent the distal end 144 of the positioning member 140, as shown in FIG. 2B. In this alternative, the pusher member 130 and positioning member 140 may include cooperating features, such as element 137 and reduced region 145 to prevent proximal movement of the pusher member 130 relative to the positioning member 140. Alternatively, the pusher member 130 may be otherwise fixed relative to the positioning member 140, for example, mechanically bonded, chemically bonded, interference fit, and the like. Thus, the distal end 134 of the pusher member 130 may be fixed a predetermined distance proximal to the positioning element 146, e.g., to provide the plug 2 immediately adjacent the positioning element 146, as shown in FIG. 2B. Additional information on such alternatives and methods for making and using them may be found in co-pending application Ser. No. 60/825,410, filed Sep. 13, 2006, the entire disclosure of which is expressly incorporated by reference.

Figure 3A:
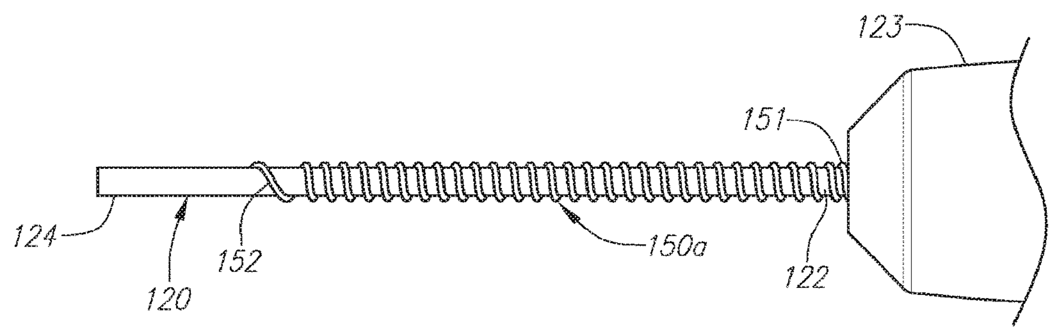
FIGS. 3A-3D are side views of the system of FIG. 1B, showing a first embodiment of a locking element for coupling the cartridge to an introducer sheath.

With additional reference to FIGS. 3A-3D, in one embodiment, the locking element 150 on the cartridge 120 may be a coil or spring lock 150*a* disposed over the cartridge 120. Initially, the coil 150*a* may extend circumferentially around the cartridge 120 from the hub 123 towards the distal end 124, as shown in FIG. 3A. Optionally, a proximal end 151 of the coil 150*a* may be attached or otherwise secured to the hub 123, e.g., to prevent rotation and/or distal migration of the proximal end 151. Alternatively, the proximal end 151 of the coil 150*a* may simply abut the hub 123, e.g., due to the diameter of the coil 150*a* being smaller than the diameter of the hub 123. The coil 150*a* may have a leading end 152, which may end in one or more windings extending more axially than other windings 154, e.g., those extending from the leading end 152 to the proximal end 151. For example, as shown, the leading end 152 may terminate in a loose wire tip extending towards the distal end 124 of the cartridge 120, e.g., which may be shaped into a rounded or hook shape. Alternatively, the leading end 152 may extend around the cartridge 120, e.g., including one or more windings that extend radially around the distal end 124 of the cartridge 120, i.e., substantially perpendicular to a longitudinal axis of the cartridge 120.

Figure 3B:
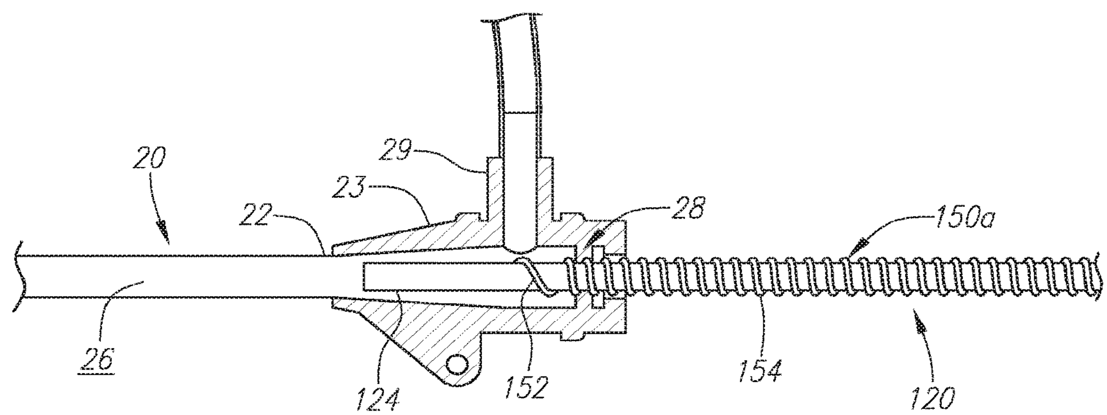
Figure 3C:
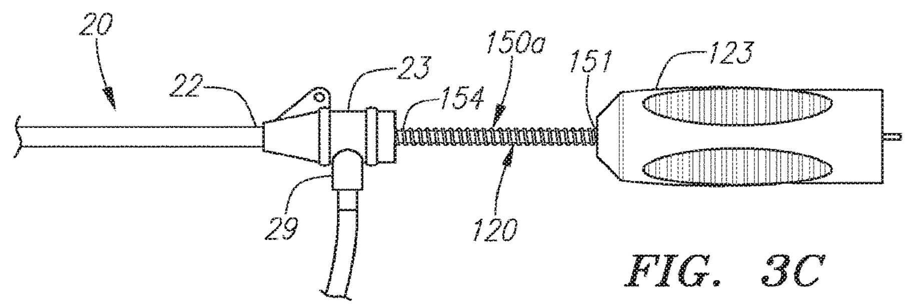

As shown in FIG. 3B, the diameter of the leading end 152 of the coil 150*a* may be sufficiently small to allow the leading end 152 to enter into the opening 27 in the hub 23 of the introducer sheath 20. The axially extending tip may facilitate initially passing the leading end 152 through the opening 27 and past the abutment(s) 28 therein. Most or all of the adjacent windings 154 may be oriented more radially (or substantially perpendicularly relative to the longitudinal axis) around the cartridge 120, e.g., to engage the abutment 28 as the coil 150*a* is advanced through the opening 27, as shown in FIG. 3C. The engagement of the windings 154 of the coil 150*a* to the abutment 28 may substantially couple the introducer sheath 20 to the cartridge 120, e.g., to subsequently couple movement of the introducer sheath 20 to movement of the cartridge 120.

Figure 3D:
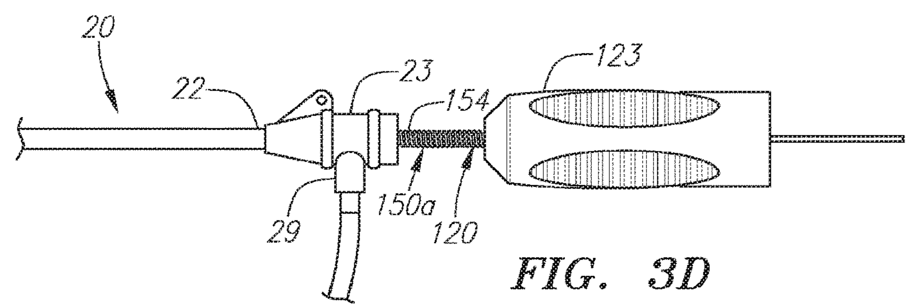

When the introducer sheath 20 and the cartridge 120 are coupled by the coil 150*a* in this manner, the cartridge 120 may still be advanced distally through the coil 150*a* and further into the introducer sheath 120. Additionally, the diameter of the hub 123 may be greater than the diameter of the coil 150*a*, such that the hub 123 compresses the coil 150*a* as the cartridge 120 is advanced distally into the introducer sheath 120, as shown in FIG. 3D.

The coil 150*a* may allow the cartridge 120 to be engaged with introducer sheaths having different lengths. For example, as shown in FIG. 3C, when the cartridge 120 is advanced into a relatively short introducer sheath, e.g., having a length of twelve centimeters (12 cm), the coil 150*b* may be only slightly compressed by the time the distal end 124 of the cartridge 120 contacts the expanded positioning element 146, as described further elsewhere herein. Alternatively, as shown in FIG. 3D, when the cartridge 120 is advanced into a relatively long introducer sheath, e.g., having a length of fifteen centimeters (15 cm), the coil 150*a* may be axially compressed further by the time the distal end 124 of the cartridge 120 contacts the expanded positioning element 146. In either case, sufficient windings may engage the abutment(s) 28 to couple the introducer sheath to the cartridge 120. In addition or alternatively, the lengths of the coil 150*a* and the cartridge 120 may be sized relative to one another such that the coil 150*a* becomes incompressible or provides substantial resistance to further advancement, e.g., to provide tactile feedback to the user, before the cartridge 120 exits the introducer sheath through the distal end 24. This may prevent the sealant 2 from being advanced beyond the introducer sheath 20, e.g., into a blood vessel or other body lumen communicating with the puncture.

Thereafter, when the cartridge 120 is retracted proximally, the leading end 152 of the coil 150*a* may engage the abutment(s) 28, thereby pulling the introducer sheath 20 proximally with the cartridge 120. The windings of the leading end 152 distally beyond the abutment(s) 28 may have sufficient rigidity to allow the introducer sheath 20 to be pulled proximally, and/or may be supported by the proximal windings 154 compressed against the abutment(s) 28, as shown in FIG. 3D. Optionally, if desired or necessary to disengage the coil 150*a* from the introducer sheath 20, the cartridge 120 may be rotated to unscrew the leading end 152 of the coil 150*a* from the abutment(s) 28. Thus, once disengaged, the cartridge 120 may then be retracted proximally while the introducer sheath 20 remains in place.

Turning to FIGS. 8A-9D, an exemplary method is shown for sealing a puncture 90, e.g., using the apparatus 101 described above to deliver a sealant 2, e.g., to achieve hemostasis within the puncture 90. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath 20 may be advanced through the puncture 90 into the vessel 94, e.g., over a guide wire placed through the puncture 90 into the vessel 94. The introducer sheath 20 may provide access into the vessel 92 for one or more instruments, e.g., to allow one or more diagnostic and/or interventional procedures to be performed via the vessel 92. Upon completing the procedure(s) via the vessel 94, any such instrument(s) may be removed from the puncture 90, leaving the introducer sheath 20 extending through the puncture 90 into the vessel 94.

Figure 8A:
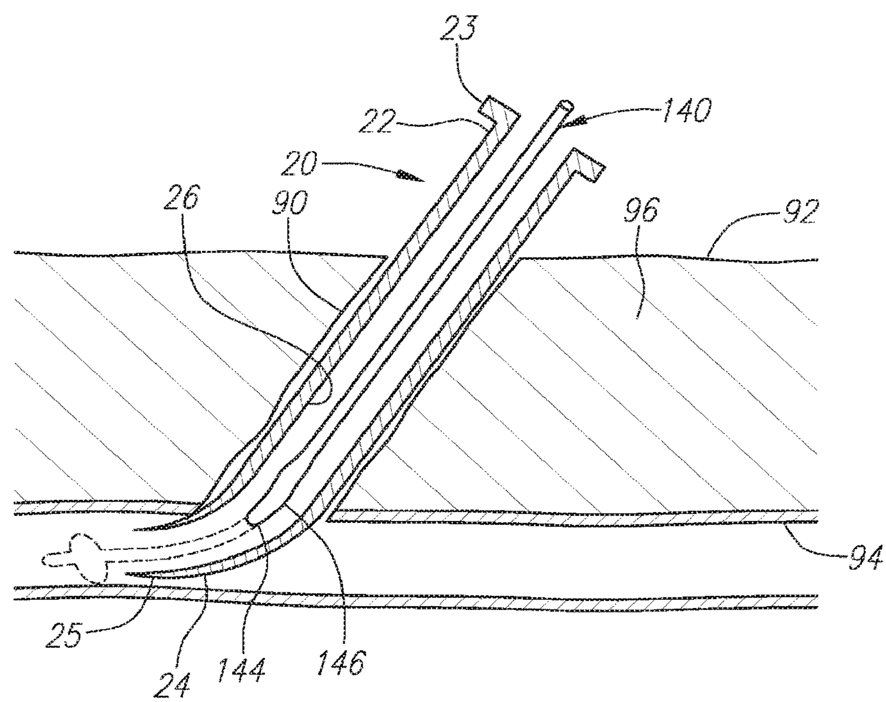
FIGS. 8A and 8B are cross-sectional views of a patient's body, showing a method for delivering a temporary occlusion or positioning member through an introducer sheath into a puncture extending from a patient's skin to a blood vessel using the system of FIG. 1B.

With reference to FIG. 8A, a positioning member 140 may be introduced into and/or through the lumen 26 of the introducer sheath 20, e.g., with the expandable positioning element 146 in a collapsed condition. The cartridge 120, along with the sealant 2 and pusher member 130, may be provided initially on the proximal end 142 of the positioning member 140 (not shown in FIG. 8A for clarity, see FIG. 1A). Thus, the distal end 124 of the cartridge 120 may initially be located outside the puncture 90 when the positioning member 30 is advanced into the puncture 90. Alternatively, the cartridge 120 may be carried on the distal end 144 of the positioning member 140, e.g., as shown in FIG. 2B, such that the cartridge 120 (along with the sealant 2 and pusher member 130) are introduced simultaneously with the positioning member 140, as described in application Ser. No. 60/825,410, incorporated by reference herein.

Figure 8B:
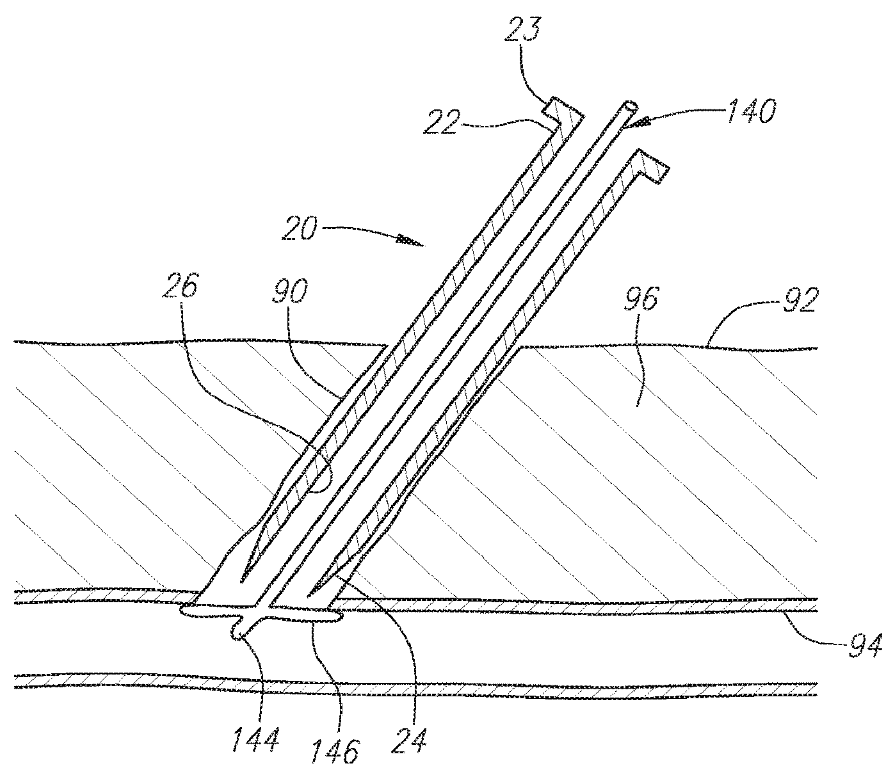

Still referring to FIG. 8A, the distal end 144 of the positioning member 140 may be inserted through the puncture 90 (via the introducer sheath 20) and into the vessel 94 (shown in phantom). Once the positioning element 146 is disposed within the vessel 94, i.e., beyond the distal end 24 of the introducer sheath 20, the positioning element 146 may be expanded to an enlarged condition, e.g., as shown in FIG. 8B. After expanding the positioning element 146, the positioning member 140 may be at least partially withdrawn until the positioning element 146 contacts the wall of the vessel 94, e.g., to substantially seal the vessel 94 from the puncture 90.

In an exemplary method, this may involve a two-step process (although it may be completed in a single continuous action). First, with the positioning element 146 expanded within the vessel 94, the positioning member 140 may be withdrawn until the positioning element 146 contacts the distal end 24 of the introducer sheath 20, which may provide a first tactile feedback to the user (i.e., that the positioning element 146 has contacted the introducer sheath 20, e.g., based upon the increased weight and/or resistance to proximal movement). The positioning member 140 may be withdrawn further until the positioning element 146 contacts the wall of the vessel 94 and resists further withdrawal, thereby providing a second tactile feedback. The introducer sheath 20 may be pulled proximally by the positioning element 146 as the positioning member 120 is withdrawn, e.g., until the distal end 24 of the introducer sheath 20 is withdrawn from the vessel 94 into the puncture 90, as shown in FIG. 8B.

Proximal tension may be applied and/or maintained on the positioning member 140 to hold the positioning element 146 against the wall of the vessel 94, e.g., to seal the puncture 90 from the vessel 94 and/or prevent further removal of the positioning member 140. The proximal tension may be maintained manually or using a tensioner device (not shown) to provide temporary hemostasis, e.g., during the subsequent steps. Exemplary tension devices are disclosed in co-pending application Ser. No. 10/806,952, filed Mar. 22, 2004, the entire disclosure of which is expressly incorporated herein by reference.

Figure 9A:
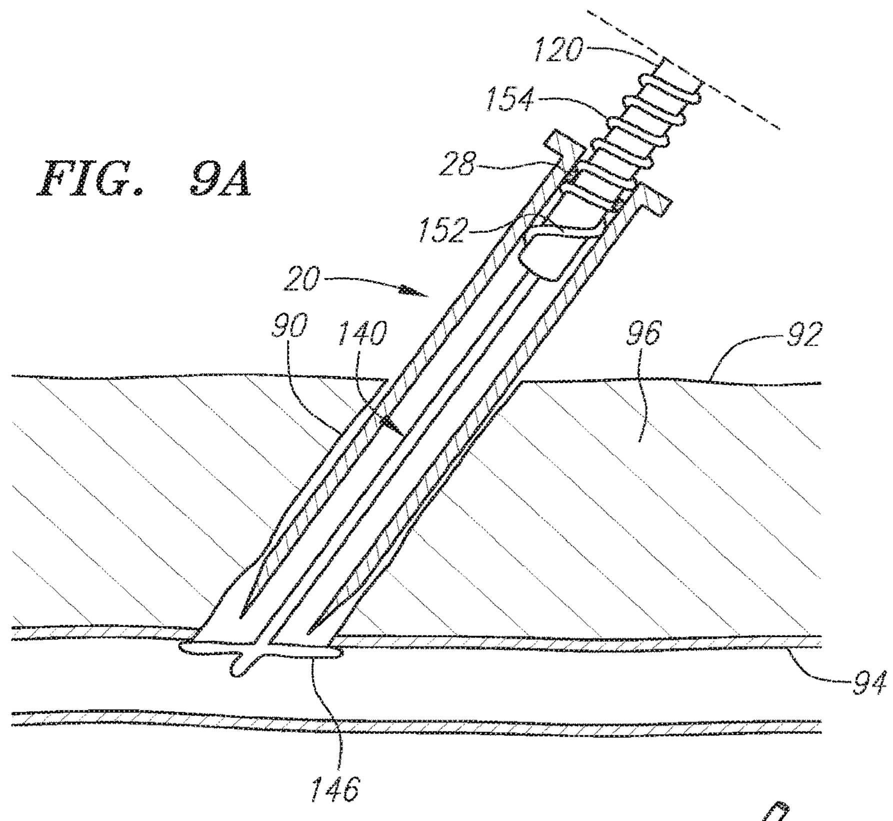
FIGS. 9A-9D are cross-sectional views of a patient's body, showing a method for sealing a puncture extending from the patient's skin to a blood vessel using the apparatus of FIGS. 3A-3D introduced into the introducer sheath and over the positioning member of FIGS. 8A and 8B.
Figure 9B:
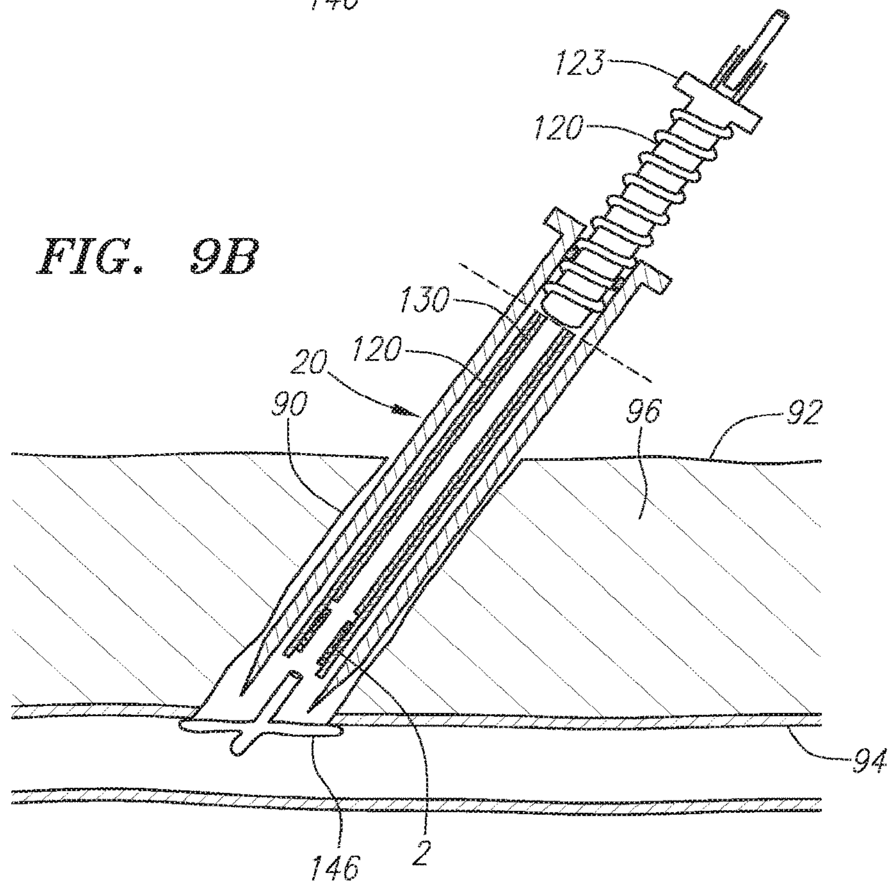

Turning to FIGS. 9A and 9B, the cartridge 120 (carrying the sealant 2) may be advanced distally over the positioning member 140 into the puncture 90. For example, FIG. 9A illustrates the cartridge 120 and locking element 150 of FIG. 3A being advanced distally over the positioning member 140 and into the introducer sheath 20. The leading end 152 of the coil 150*a* is advanced through or beyond the abutment 28, after which the subsequent windings 154 of the coil 150*a* engage the abutment 28, as shown in FIG. 9A. The cartridge 120 thus becomes coupled to the introducer sheath 20, thereby coupling subsequent movement of the introducer sheath 20 to that of the cartridge 120. The cartridge 120 may be further advanced into the introducer sheath 20 toward the positioning element 146, e.g., compressing the coil 150*a*, as shown in FIGS. 9B, 3C, and 3D.

Figure 9C:
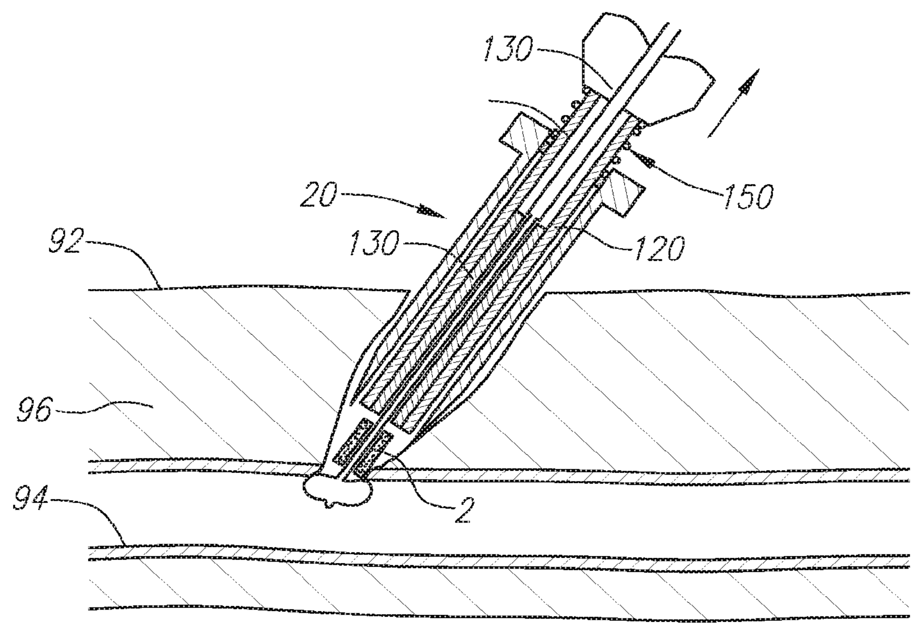

Thereafter, the cartridge 120 may be retracted, e.g., by pulling proximally on the hub 123. Because the locking element 150 has coupled the introducer sheath 20 to the cartridge 120, this action also withdraws the introducer sheath 20 from the puncture 90. As the cartridge 120 is retracted, the pusher member 130 may prevent substantial proximal movement of the sealant 2, thereby exposing the sealant 2 within the puncture 90, as shown in FIG. 9C. For example, as described above with reference to FIGS. 2A and 2B, as the cartridge 120 is advanced, the pusher member 130 may pass over the reduced region 145 of the positioning member 140, as shown in FIG. 2B. When the cartridge 120 is then retracted, the element 137 on the pusher member 130 may abut the reduced region 145, thereby preventing substantial proximal movement of the pusher member 130, and the sealant 2 adjacent the distal end 134 of the pusher member 130.

When the sealant 2 is exposed within the puncture 90, the sealant 2 may be exposed to blood and/or other body fluids within the puncture 90. This exposure may cause the sealant 2 to absorb fluid and/or otherwise expand within the puncture 90, e.g., to provide hemostasis. If desired, once the sealant 2 is exposed within the puncture 90, the pusher member 130 may be advanced to compress or tamp the sealant 2, e.g., against the positioning element 146. Optionally, the pusher member 130 may include one or more distance markers (not shown) on or adjacent the proximal end 132, and the pusher member 130 may be advanced into the puncture 90 a desired distance, which may be confirmed by monitoring the distance markers.

Figure 9D:
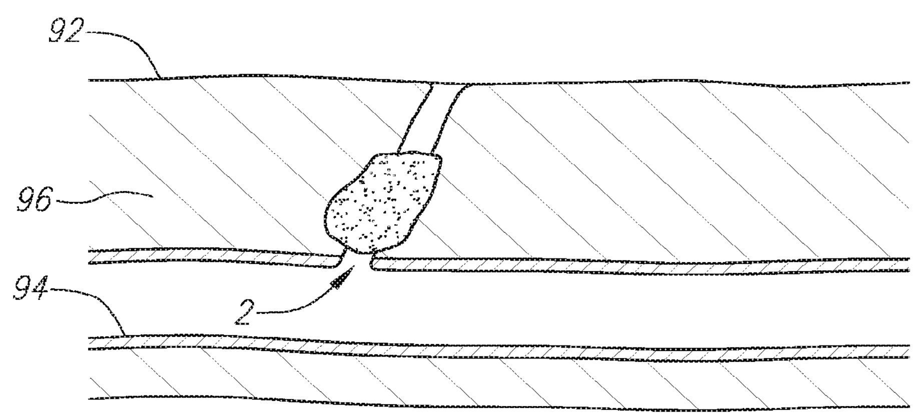

Once the sealant 2 has been exposed for sufficient time and/or tamped by the pusher member 130, the positioning element 146 may be collapsed, and the positioning member 140 withdrawn from the vessel 94 and puncture 90, e.g., pulling the collapsed positioning element 146 through the sealant 2 and pusher member 130. The pusher member 130 may be maintained substantially stationary during withdrawal of the positioning member 140, e.g., to prevent migration and/or dislodgment of the sealant 2 within the puncture 90. Once the positioning member 140 is completely removed, the pusher member 130 may be removed from the puncture 90, leaving the sealant 2 within the puncture 90, as shown in FIG. 9D.

Optionally, after removing the positioning member 140, liquid hydrogel or other sealing compound, or other material may be delivered into the puncture 90, e.g., above and/or around the sealant 2, to assist in achieving hemostasis. For example, such material may be delivered via the lumen 136 of the pusher member 130 and/or by introducing another delivery device (not shown) into the puncture 90, e.g., after removing the pusher member 130.

Figure 4A:
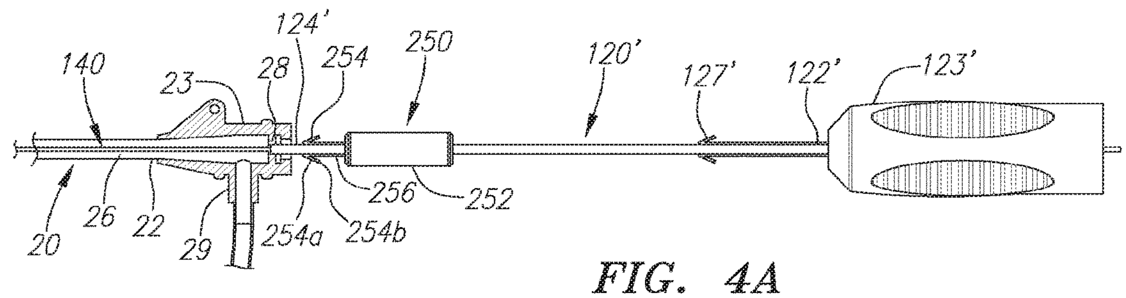
FIGS. 4A-4D are side views of an alternative embodiment of the system of FIG. 1B, showing another embodiment of a locking element for coupling the cartridge to an introducer sheath.
Figure 4B:
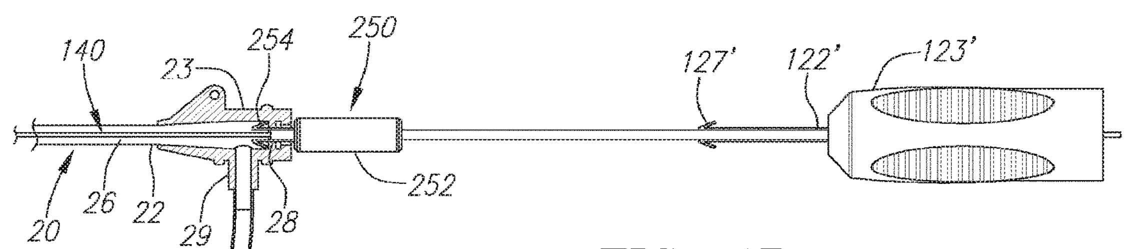
Figure 4C:
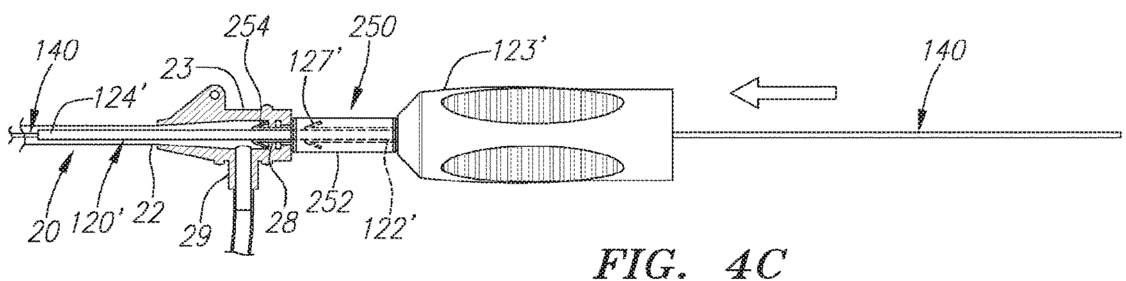
Figure 5A:
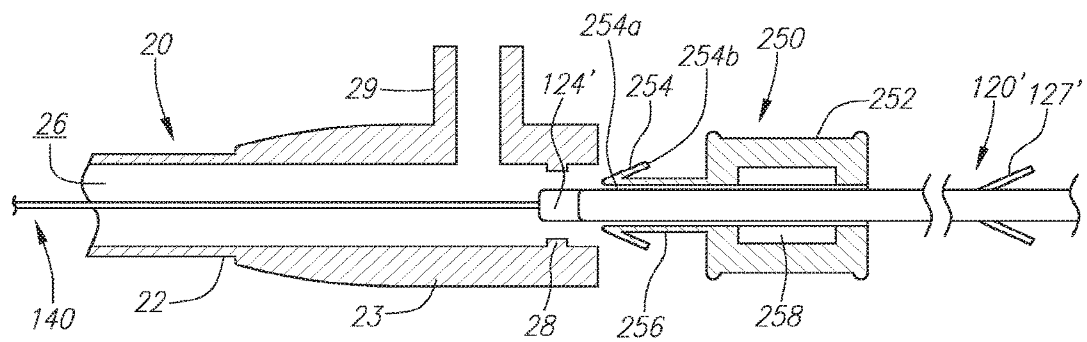
FIGS. 5A-5C are cross-sectional details of the system of FIGS. 4A-4D, showing the locking element coupling the introducer sheath to the cartridge.
Figure 5B:
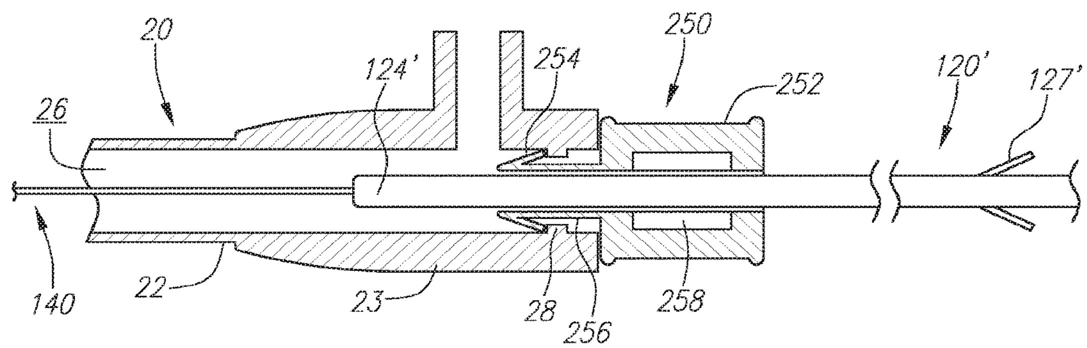
Figure 5C:
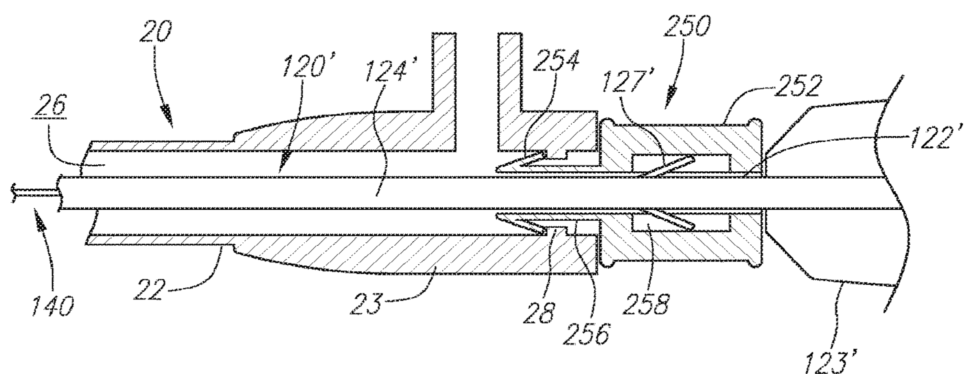

Turning to FIGS. 4A-4C and 5A-5C, another embodiment of a locking element 250 is shown that may be carried by a cartridge 120' of an apparatus 101,' which may be similar to other embodiments described herein. Generally, the locking element 250 includes a sleeve or other carrier 252 and a first set of one or more barbs, catches, detents, or other features 254 extending from the sleeve 252. As best seen in FIGS. 5A-5C, the first detents 254 may be provided on a nipple or other extension 256 extending distally from the sleeve 252. The extension 256 may have a size smaller than the sleeve 252, e.g., such that the extension 256 and first detents 254 may be received in a hub 23 of an introducer sheath 20, while the sleeve 252 abuts the hub 23, as described further below. The first detents 254 may be biased to extend outwardly from the sleeve 252, e.g., diagonally or otherwise laterally, to define an expanded position. Yet, the first detents 254 may be compressible radially inwardly toward the sleeve 252 to define a compressed position, the first detents 254 resiliently returning to the expanded position when free from external forces. As shown, the first detents 254 may include sloped distal edges 254*a* to facilitate compressing the first detents 254, e.g., as they enter the opening 27 and pass through the abutment(s) 28, and substantially blunt proximal ends 254*b* that may contact the abutment(s) 28 to prevent removal of the first detents 254 from the introducer sheath 20.

The sleeve 252 also has a passage 258 extending therethrough that allows the sleeve 252 to slidably receive the cartridge 120' therethrough. The sleeve 252 may include one or more recesses and/or catches adjacent the passage 258, which may be engaged by a second set of detents 127' on the cartridge 120,' as described further elsewhere herein. The locking element 250 may be formed from one or more pieces of material, e.g., integrally formed from a single piece by injection molding, machining, and the like. The locking element 250 may be formed from plastic, metal, or composite material such that the sleeve 252 and extension 256 are substantially rigid, while the first detents 254 are resiliently deflectable between the expanded and collapsed positions.

As best seen in FIG. 4A, the cartridge 120' generally includes a proximal end 122,' a distal end 124' sized for introduction into an introducer sheath 20, and a hub 123' on the proximal end 122,' similar to other embodiments herein. The cartridge 120' may also include a lumen (not shown) extending between the proximal and distal ends 122,' 124' within which a sealant and/or pusher member (not shown) may be disposed, also similar to other embodiments herein. Unlike other embodiments, the cartridge 120' includes a second set of one or more barbs, catches, or other detents 127' adjacent the proximal end 122' and/or hub 123.' The second detents 127' may be biased to an extended position, but resiliently compressible to a compressed position similar to the first detents 254. The second detents 127' may be integrally formed on the cartridge 120' a predetermined distance from the hub 123.' For example, the cartridge 120' and detents 127' may be injection molded together, or the detents 127' may be attached to the cartridge 120' at a desired location, e.g., by bonding with adhesive, interference fit within a recess in the cartridge 120,' sonic welding, and the like.

Before use, the locking element 250 may be carried on the distal end 124' of the cartridge 120,' as shown in FIG. 4A. For example, the sleeve 252 may be releasably attached to the cartridge 120,' e.g., using a low bond adhesive, interference fit that provides a slight degree of friction, and the like. Thus, the sleeve 252 may be slidable relative to the cartridge 120,' e.g., by overcoming the adhesive or friction, as described further elsewhere herein.

The extension 256 and first detents 254 are sized to be distally advanced into the opening 27 in the introducer sheath 20, e.g., until the first detents 254 contact the abutment(s) 28, whereby further advancement compresses the first detents 254 radially inwardly as the first detents 254 pass through the abutment(s) 28. When the first detents 254 are advanced distally beyond the abutment(s) 28, the first detents 254 may resiliently resume the expanded position, as shown in FIGS. 4C and 5B. As shown, the diameter of the first detents 254 in the expanded position is greater than the diameter within the abutment(s) 28. Thus, when the first detents 254 are in the expanded position distally beyond the abutment(s) 28, proximal movement of the locking element 250 causes the first detents 254 to engage the abutment(s) 28, coupling the introducer sheath 20 to the locking element 250 such that proximal movement of the locking element 250 causes corresponding proximal movement the introducer sheath 20.

Figure 10A:
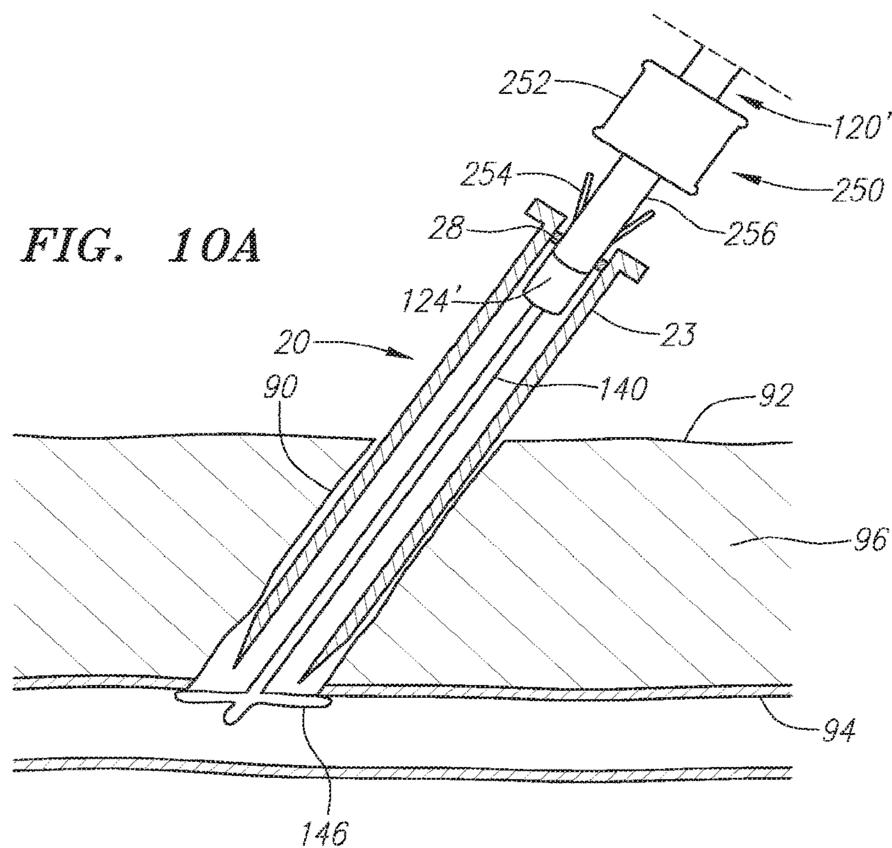
FIGS. 10A and 10B are cross-sectional views of a patient's body, showing another method for sealing a puncture extending from the patient's skin to a blood vessel using the apparatus of FIGS. 4A-4C.
Figure 10B:
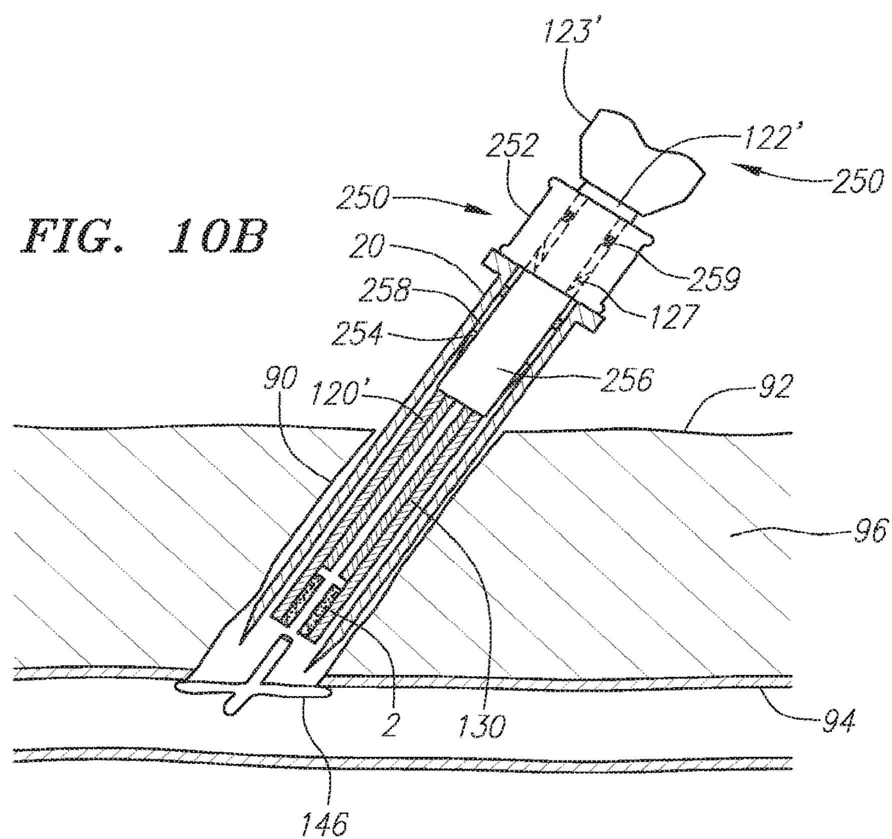

As shown in FIGS. 4A-4D, the locking element 250 may "float" somewhat on the cartridge 120.' For example, with additional reference to FIGS. 10A and 10B, when the cartridge 120' is advanced relative to the positioning member 140 and introducer sheath 20, e.g., as described in the methods above, the locking element 250 may also be advanced until the extension 256 and first detents 254 enter the introducer sheath 20 and the first detents 254 pass beyond abutment(s) 28, as shown in FIGS. 4B and 10A. Further advancement of the cartridge 120' may cause the sleeve 252 to abut the hub 23 of the introducer sheath 20, thereby preventing further advancement of the locking element 250 relative to the introducer sheath 20, as shown in FIG. 10B. Thus, the cartridge 120' may then slide through the sleeve 252 and extension 256 of the locking element 250 further into the introducer sheath 20, as shown in FIGS. 4C and 5C.

Figure 4D:
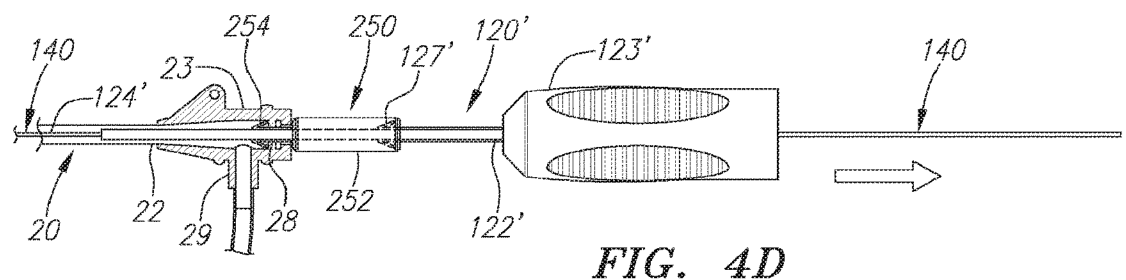

The cartridge 120' may be advanced sufficiently into the introducer sheath 20, e.g., until the distal end 124' contacts the expanded positioning element 146 (not shown, see, e.g., FIG. 8B) or the sealant 2 is otherwise positioned within the puncture 90, as described elsewhere herein. As best seen in FIGS. 5C and 10B, during this advancement of the cartridge 120,' the second detents 127' may enter into the passage 258 within the sleeve 252. The second detents 127' are also sufficiently flexible to be compressed radially inwardly as they pass under the sleeve 252, yet may resiliently resume the expanded position once exposed within the passage 258. When the cartridge 120' is subsequently moved proximally, e.g., to expose the sealant 2 within the puncture 90, the second detents 127' may abut a wall 259 of the sleeve 252 adjacent the passage 258, thereby coupling the locking element 250 to the cartridge 120,' as shown in FIGS. 4D, 5C, and 10B. Optionally, the sleeve 252 may include one or more intermediate walls (not shown) within the passage 258, e.g., such that second detents 127' may ratchet under each successive wall when the cartridge 120' is advanced distally, yet abut the immediately preceding wall when the cartridge 120' is subsequently withdrawn. This may accommodate advancing the cartridge 120' into introducer sheaths 20 of varying length.

Thus, when the second detents 127' are expanded within the passage 258 and the first detents 252 are expanded beyond the abutment(s) 28, the introducer sheath 20 is coupled to the cartridge 120' by the locking element 250. Subsequent movement of the cartridge 120,' e.g., during withdrawal to expose the sealant 2, may cause corresponding movement of the introducer sheath 20 to expose the sealant 2 within the puncture 90, similar to the methods described above with respect to the embodiment of FIGS. 3A-3D and 9A-9D.

Turning to FIGS. 6A-6D, still another embodiment of a locking element 350 is shown that may be carried by a cartridge 320 of an apparatus 301, which may be generally similar to other embodiments described herein. For example, the cartridge 320 may include a proximal end 322 attached to a hub 323, and a distal end 324 sized for introduction into an introducer sheath 20. The cartridge 320 may include a sealant and/or pusher member (both not shown) therein, all similar to other embodiments herein. Unlike previous embodiments, the cartridge 320 includes a nipple or extension 328 on the proximal end 322, e.g., attached to or otherwise extending from the hub 323.

The extension 328 includes one or more barbs, catches, detents, or other features 327 extending radially outwardly from the extension 328. The detent(s) 327 may include a ramped and/or tapered distal surface 327*a* and a blunt proximal surface 327*b*, which may facilitate inserting the extension 328 at least partially into the locking element 350, similar to the second detents 127' described elsewhere with reference to FIGS. 4A-4D. Thus, the detents 327 may be expandable or otherwise deformable to allow the detents 327 to enter the locking element 350, but preventing subsequent removal, thereby coupling the locking element 350 to the cartridge 320, as described further below.

The locking element 350 includes a sleeve, hub, or other carrier 352 and a nipple or extension 356 extending from the sleeve 352. The extension 356 includes a tapered distal end 353 including one or more flanges, catches, detents, or other features 354 that extending radially outwardly from the distal end 353. The distal end 353 may be sufficiently flexible to be expandable from a contracted position, shown in FIGS. 6B and 6C to an enlarged condition, shown in FIG. 6D. The sleeve 352 includes a passage 358 through which the cartridge 320 may be slidably received, the passage 358 including a proximal wall 359 (and optionally one or more axially spaced internal walls, not shown).

Figure 6A:
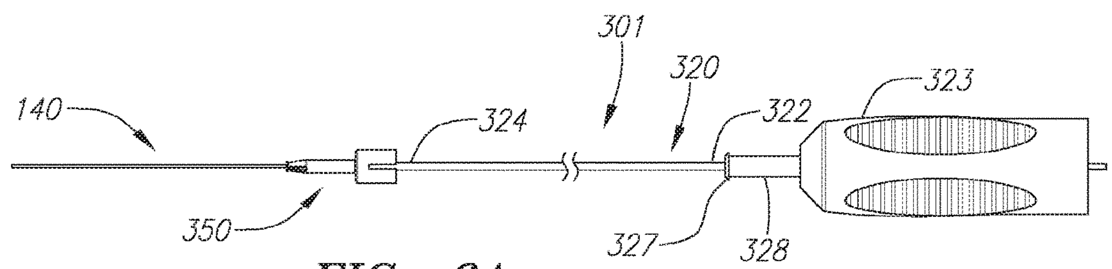
FIG. 6A is a side view of the system of FIG. 1B, showing yet another embodiment of a locking element for coupling the cartridge to an introducer sheath.
Figure 6B:
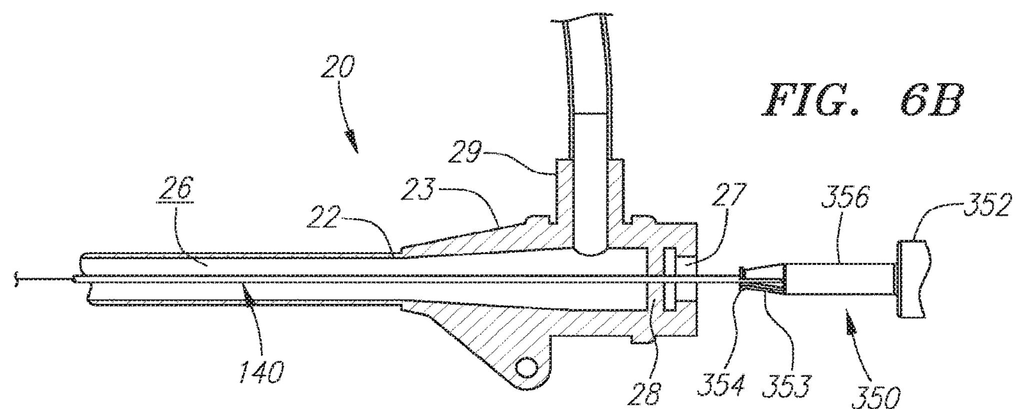
FIGS. 6B-6G are cross-sectional details of the system of FIG. 6A, showing a method for activating the locking element to coupled the introducer sheath to the cartridge.

The locking element 350 may be carried initially on the distal end 324 of the cartridge 320 with the distal end 353 in the contracted condition, as shown in FIG. 6A. For example, the locking element 350 may be releasably secured to the cartridge 120, e.g., using an adhesive, an interference fit, and the like, which may be disrupted when an axial force is applied to the cartridge 320. The passage 358 may be sized to slidably receive the distal end 324 of the cartridge 320 therethrough, while the distal end 353 of the extension 356 is tapered in the contracted position to a cross-section smaller than the distal end 324 of the cartridge 320. In the contracted condition, the distal end 353 and detent(s) 354 are sized to be received through the opening 27 of the introducer sheath 20, as shown in FIG. 6B.

Figure 6C:
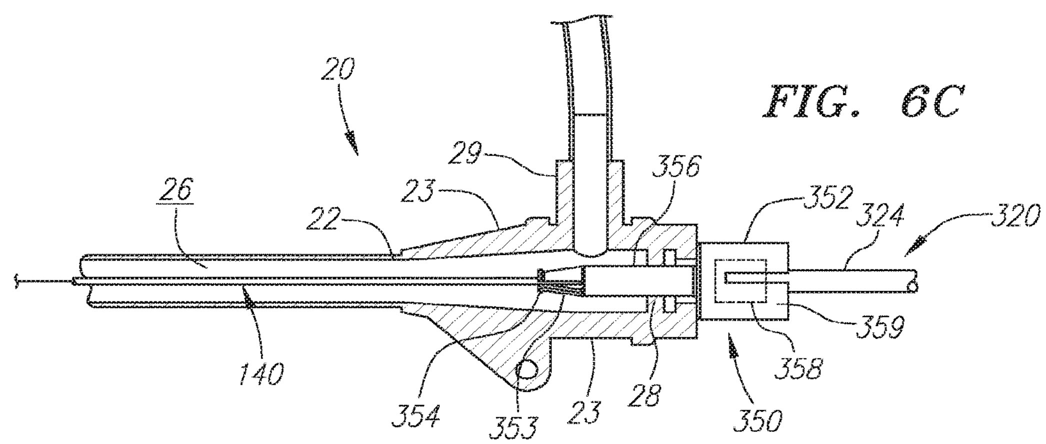
Figure 6D:
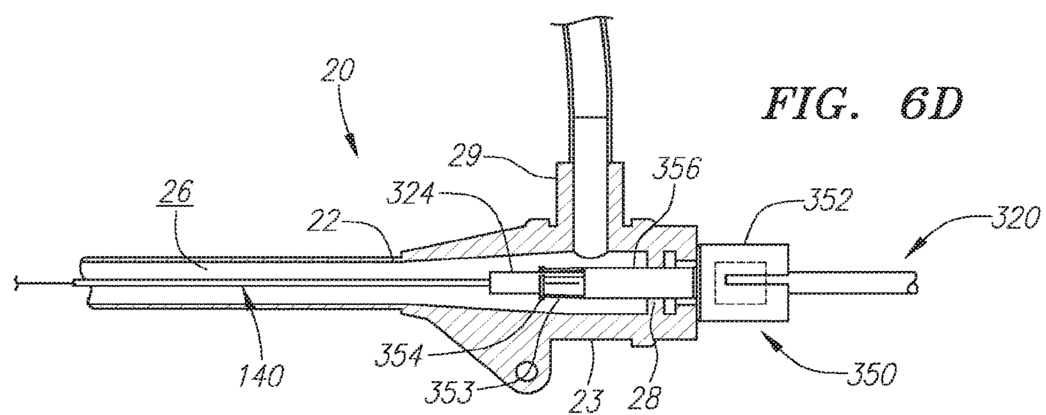

When the cartridge 320 is advanced distally through the sleeve 352 and into the lumen 26 of the introducer sheath 20, the cartridge 320 pushes the distal end 353 outwardly to the expanded position, as shown in FIG. 6D. The distal end 353 may be plastically deformed when directed to the expanded position, e.g., such that the distal end 353 remains in the expanded position even if the cartridge 320 is subsequently removed therefrom, or the distal end 353 may be sufficiently elastic to resiliently return towards the contracted position if the cartridge 320 is removed therefrom.

In the expanded position, the diameter of the detent(s) 354 on the distal end 353 is greater than that of the abutment(s) 28 in the introducer sheath 20. Thus, when the tube distal end 353 of the extension 356 is advanced into the hub 23 of the introducer sheath 20 beyond the abutment(s) 28 and directed to the expanded position, proximal movement of the locking element 350 causes the detent(s) 354 to engage the abutment 28, coupling the locking element 350 to the introducer sheath 20 and limiting proximal movement of the introducer sheath 20 separately from the locking element 350. When the locking element 350 is also coupled to the cartridge 320, subsequent proximal movement of the introducer sheath 20 is thus coupled to proximal movement of the cartridge 120, similar to the other embodiments herein.

The diameter of the sleeve 352 of the locking element 350 may be greater than that of the lumen 26 of the introducer sheath 20, such that the sleeve 352 cannot enter the lumen 26, thereby limiting advancement of the extension 356, distal end 353, and detent(s) 354 into the introducer sheath 20. Thus, the locking element 350 may be advanced distally into the introducer sheath 20 until the sleeve 352 abuts the hub 23 of the introducer sheath 20, preventing the extension 356 from advancing further into the introducer sheath 20. The cartridge 320 may still be advanced through the locking element 350 when the sleeve 352 contacts the hub 23 of the introducer sheath 20 to automatically expand the distal end 353 and detent(s) 354 of the locking element 350.

The locking element 350 may be coupled to the cartridge 320 when the cartridge 320 is advanced distally through the locking element 350 into the introducer sheath 20. For example, when the cartridge 320 is advanced into the introducer sheath, the locking element 350 may be advanced into the hub 23 of the introducer sheath until the distal end 353 and detent(s) 354 are disposed distally beyond the abutment(s) 28, as described above. When the sleeve 352 of the locking element 350 abuts the hub 23, the cartridge 320 may continue to be advanced through the locking element 350 until the detent(s) 327 on the cartridge 320 pass under the sleeve 352 and enter the passage 358 therein. The tapered distal end 327*a* may facilitate passing the detent(s) 327 under the sleeve 352, while the blunt proximal end 327*b* may abut the internal wall 359 to prevent subsequent disengagement of the locking element 350 from the cartridge 320. Optionally, the hub 323 of the cartridge 120 may be larger than the sleeve 352 of the locking element 350, thereby limiting distal movement of the cartridge 320 relative to the locking element 350.

Thus, when the detent(s) 327 on the cartridge 320 enter the passage 358 within the sleeve 352, subsequent proximal movement of the cartridge 320 causes corresponding proximal movement of the locking element 350. This couples subsequent movement of the introducer sheath 20 to that of the cartridge 320.

Figure 11A:
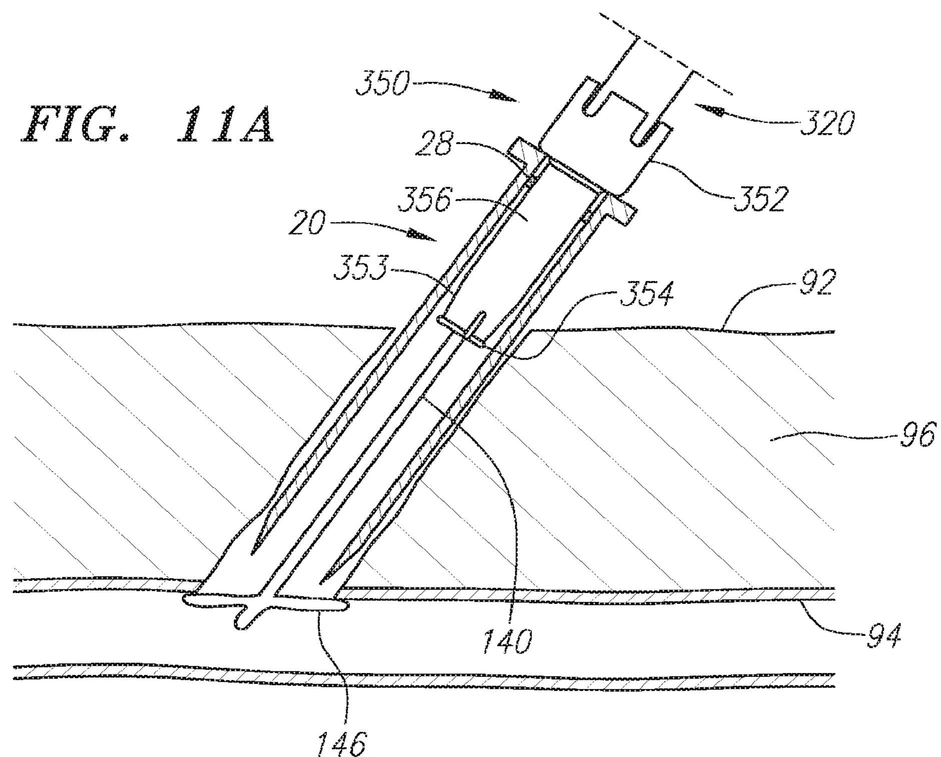
FIGS. 11A and 11B are cross-sectional views of a patient's body, showing still another method for sealing a puncture extending from the patient's skin to a blood vessel using the apparatus of FIGS. 6A-6D.
Figure 11B:
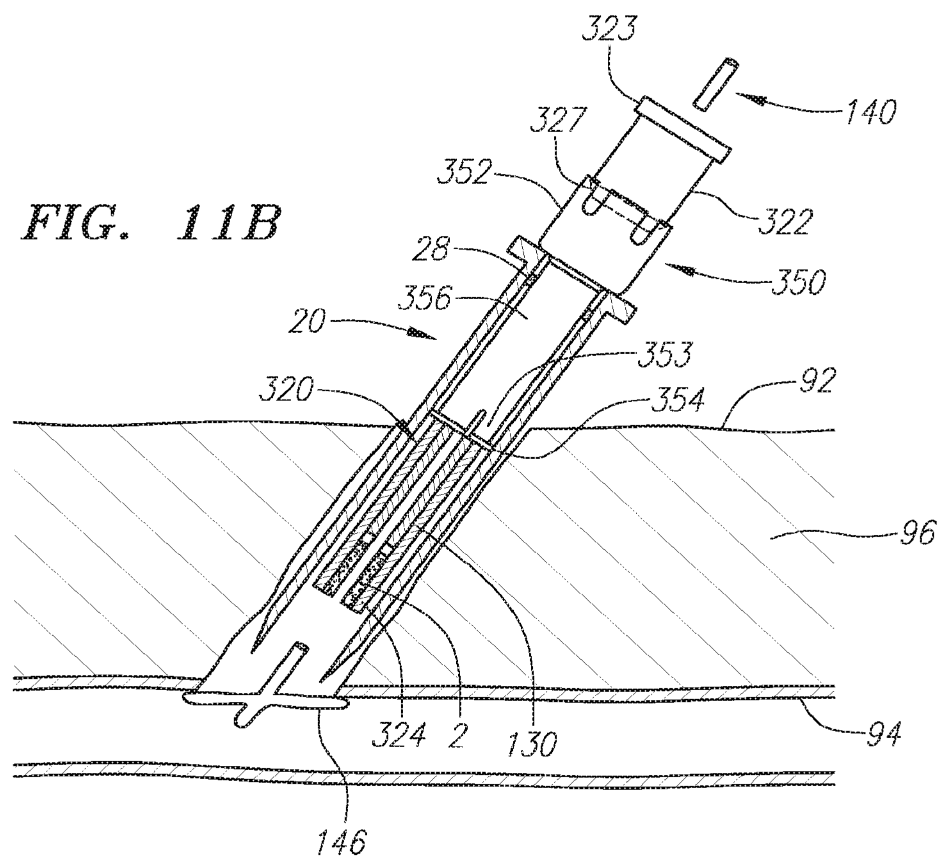

During use, the apparatus 301 may be used to deliver sealant 2 within a puncture 90, similar to other embodiments described elsewhere herein. For example, as shown in FIGS. 11A and 11B, an introducer sheath 20 may be disposed from a patient's skin 92, through a puncture 90 into a body lumen 94, similar to other methods herein. With the positioning element 146 collapsed (not shown), the positioning member 140 may be advanced through the introducer sheath 20, the positioning element 146 expanded, and retracted against the wall of the body lumen 94, also as shown in FIG. 11B. The cartridge 320 may then be advanced over the positioning member 140 into the introducer sheath 20, as shown in FIGS. 6B-6F, 11A, and 11B.

As shown in FIGS. 6B and 11A, the locking element 350 is advanced in front of the cartridge 320 into the introducer sheath 20 with the distal end 353 remaining in the contracted condition. Once the sleeve 353 of the locking element 350 abuts the hub 23 of the introducer sheath 20, advancement of the locking element 350 is stopped, while the cartridge 320 is continued to be advanced (optionally breaking any adhesive and/or severing any other connection between the cartridge 320 and the locking element 350). At this stage, the distal end 353 and detent(s) 354 of the locking element 350 are disposed distally beyond the abutment(s) 28 of the introducer sheath 20, as best seen in FIG. 6C. As the distal end 324 of the cartridge 320 passes through the locking element 350 during further advancement, the cartridge 320 causes the distal end 353 and the detent(s) 354 to expand outwardly to the expanded position, as shown in FIGS. 6D and 11B.

Figure 6E:
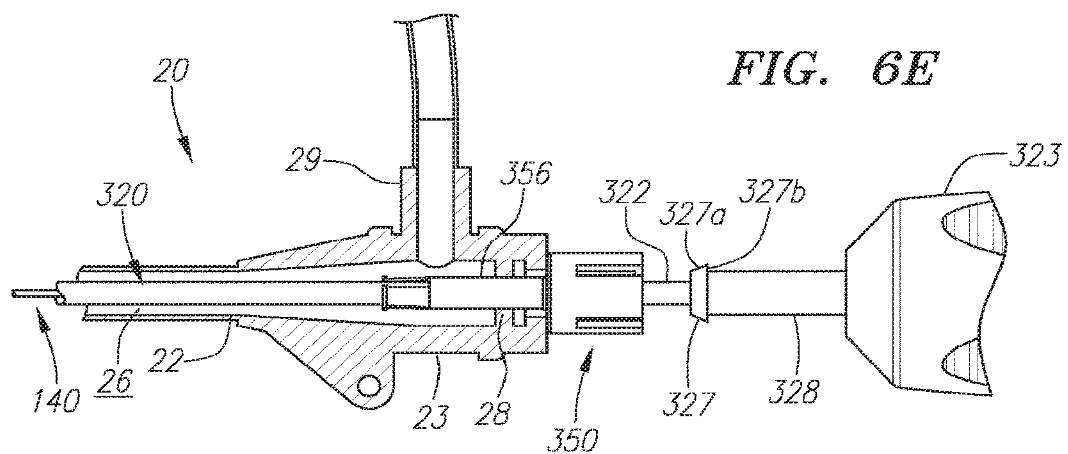
Figure 6F:
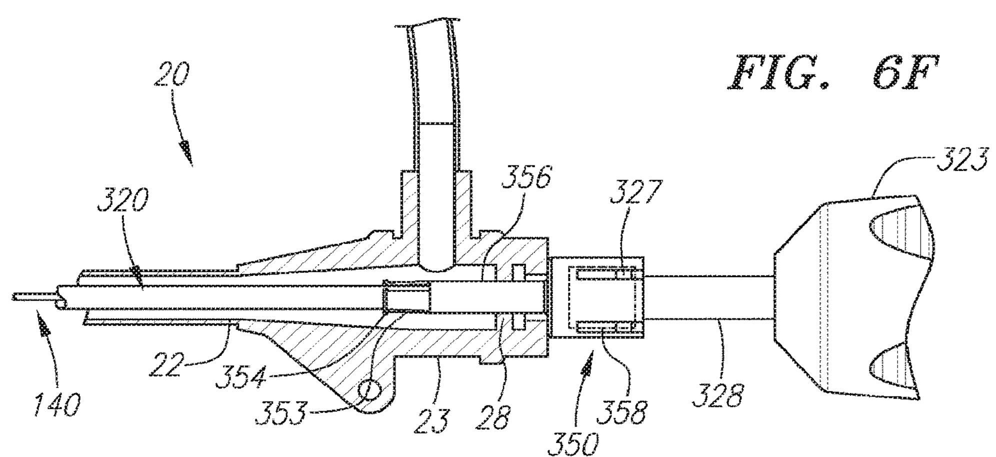

The cartridge 320 may continue to be advanced distally toward the positioning element 146 until the detent(s) 327 on the cartridge 320 pass under the sleeve 352 and enter the passage 358, as shown in FIGS. 6E and 6F. Optionally, distal advancement of the cartridge 320 may be limited by the hub 323 abutting the sleeve 352 of the locking element 350. Once in this position, the introducer sheath 20 is coupled to the locking element 350, which is, in turn, coupled to the cartridge 320.

Figure 6G:
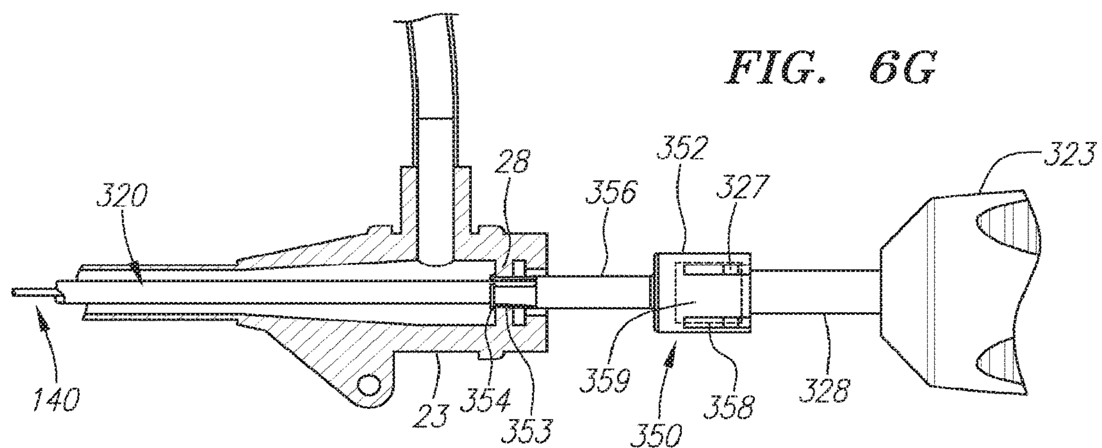

Subsequently, as shown in FIG. 6G, proximal movement of the cartridge 320 causes the detent(s) 327 to engage the wall 359 within the passage 358 of the sleeve 350, thereby causing corresponding proximal movement of the locking element 350. This movement, in turn, causes the detent(s) 354 of the locking element 350 to engage the abutment(s) 28 within the introducer sheath 20, thereby causing corresponding proximal movement of the introducer sheath 20. Thus, when the cartridge 320 is retracted to expose the sealant 2, as shown in FIG. 11B, the introducer sheath 20 may also be retracted such that the sealant 2 is exposed within the puncture 90 itself, e.g., similar to the embodiment shown in FIGS. 9C and 9D.

Figure 7A:
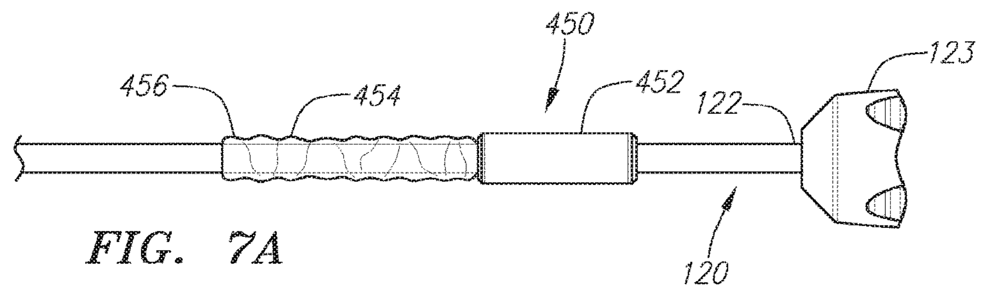
FIG. 7A is a side view of another embodiment of a locking element carried by a cartridge.

Turning to FIGS. 7A-7D, still another embodiment of a locking element 450 is shown that may be provided on a cartridge 120, which may be similar to other embodiments described elsewhere herein. In this embodiment, as best seen in FIG. 7A, the locking element 450 includes a expandable bellows or sleeve 454 including a hub or collar 452 on a proximal end, and a distal end 456 fixed axially relative to the cartridge 120. The bellows 454 may be formed from a flexible thin-walled tubing, e.g., a section of heat-shrink tubing that has been shrunk over a mandrel having a desired pattern of undulations, e.g., a screw or other helically threaded mandrel (not shown). The locking element 450 may be provided around the cartridge 120 with the distal end 456 fixed and the collar 120 loose or releasable secured thereto. For example, the distal end 456 may be substantially permanently attached to the cartridge 120, e.g., by bonding with adhesive, sonic welding, and the like. Optionally, the collar 452 may be bonded adjacent a proximal end 122 of the cartridge 120, but may be released, if desired, by overcoming the strength of the bond.

Figure 7B:
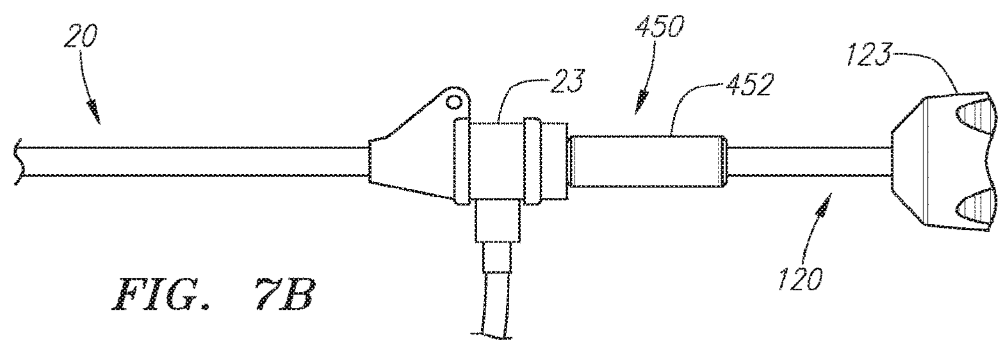
FIGS. 7B-7D are side views of the embodiment of FIG. 7A, showing the cartridge being inserted into an introducer sheath and coupling and decoupling the locking element to the introducer sheath.
Figure 7C:
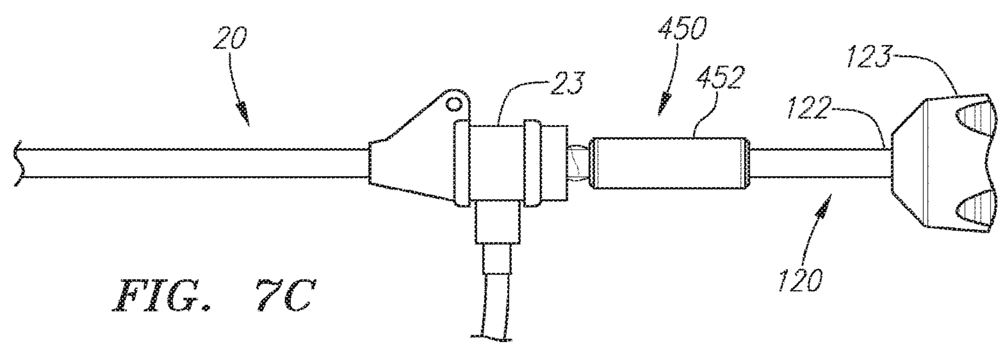

During use, when the cartridge 120 is advanced into an introducer sheath 20, as shown in FIG. 7B, the distal end 456 of the bellows 454 may enter the hub 23 of the introducer sheath 20 and pass through one or more abutments (not shown) therein, similar to previous embodiments. As the cartridge 120 is advanced, the bellows 454 may also be advanced axially, as the collar 452 is free to move over the cartridge 120 (e.g., if the collar 452 is loose or released from being secured to the cartridge 120), thereby causing the undulations of the bellows 454 to compress radially towards the cartridge 120 and advance past the abutment(s) within the introducer sheath 20. Subsequent proximal movement of the cartridge 120 causes the bellows 454 to expand radially outwardly and engage the abutment(s) within the introducer sheath 20, thereby coupling the introducer sheath 20 to the locking element 450, and consequently to the cartridge 120, as shown in FIG. 7C. Thus, subsequent retraction of the cartridge 120 may cause the introducer sheath 20 also to retract, e.g., during deployment of a sealant (not shown) carried within the cartridge 120.

Figure 7D:
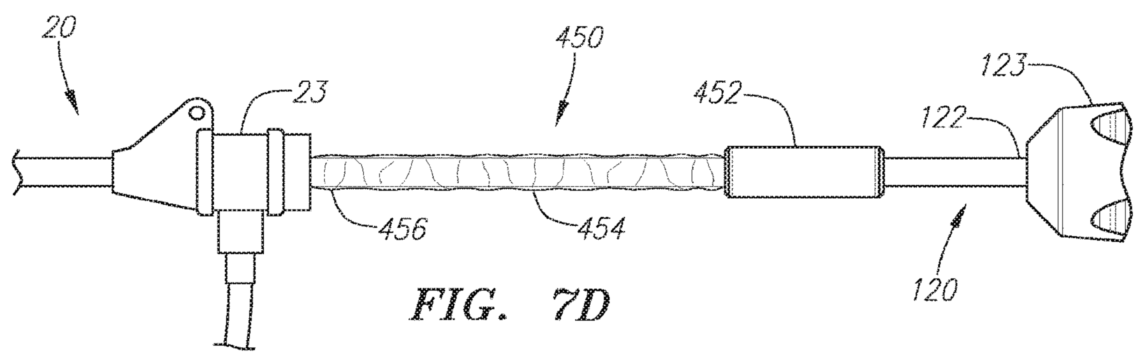

If it is desired to disengage the introducer sheath 20 from the cartridge 120, the collar 452 may be pulled proximally to collapse and extend the bellows 454 out of the hub 23 of the introducer sheath 20, as shown in FIG. 7D. With the bellows 454 radially collapsed and no longer engaging the abutment(s) within the introducer sheath 20, the cartridge 120 may be retracted independently of the introducer sheath 20.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for sealing a puncture extending through a tissue having an introducer sheath therein, comprising:
- a cartridge comprising a proximal end, a distal end sized for insertion through the introducer sheath within the puncture extending through the tissue, and a lumen extending between the proximal end and the distal end;
- a locking element on the cartridge comprising an extension that has at least one first detent, the extension and the at least one first detent sized for introduction into a lumen of the introducer sheath when the cartridge is inserted into the introducer sheath, wherein the cartridge is coupled to at least one second detent, and wherein the locking element comprises a sleeve with a passage therethrough configured to receive the at least one second detent to thereby couple the cartridge to the locking element;
- a sealant disposed within the lumen of the cartridge; and
- a pusher member disposed within the lumen of the cartridge for deploying the sealant distally from the lumen of the cartridge when the cartridge is retracted proximally relative to the pusher member.

2. The apparatus of claim 1, wherein the locking element is configured to couple the introducer sheath to the cartridge such that, when the cartridge is advanced into the lumen of the introducer sheath, a subsequent proximal movement of the cartridge causes a corresponding proximal movement of the introducer sheath such that the sealant is deployed beyond the distal end of the introducer sheath.

3. The apparatus of claim 1, wherein the at least one first detent is one or more detents are compressible radially inwardly to accommodate insertion into the lumen of the introducer sheath and resiliently expandable to an enlarged condition to engage one or more mating features within the introducer sheath.

4. A system for sealing a puncture extending through a tissue comprising:
- an introducer sheath comprising a proximal end, a distal end sized for insertion through the puncture extending through the tissue, and a lumen extending between the proximal end and the distal end of the introducer sheath;
- a tubular member comprising a proximal end, a distal end sized for insertion into the lumen of the introducer sheath, and a lumen extending between the tubular member the proximal end and the distal end of the tubular member;
- a sealant disposed within the lumen of the tubular member lumen; and
- a locking element carried on the tubular member for coupling the introducer sheath to the tubular member when the tubular member and the locking element are advanced into the lumen of the introducer sheath such that a subsequent proximal movement of the tubular member causes a corresponding proximal movement of the introducer sheath such that the sealant is deployed beyond the introducer sheath distal end of the introducer sheath, wherein the locking element comprises one or more first detents for engaging one or more mating features within the lumen of the introducer sheath when the tubular member is advanced into the introducer sheath to couple the introducer sheath to the locking element, and wherein the tubular member comprises one or more second detents for engaging an inner surface of the locking element when the tubular member is advanced into the introducer sheath to couple the locking element to the tubular member.

5. The system of claim 4, wherein the one or more first detents are compressible radially inwardly to accommodate insertion into the lumen of the introducer sheath and resiliently expandable to an enlarged condition to engage the one or more mating features within the lumen of the introducer sheath.

6. The system of claim 4, wherein the one or more first detents are carried on a sleeve on the tubular member.

7. The system of claim 6, wherein the sleeve is free to float on the tubular member.

8. The system of claim 6, wherein the locking element further comprises an extension extending distally from the sleeve, the extension sized for insertion into the lumen of the introducer sheath and the one or more first detents coupled to the extension.

9. An apparatus for sealing a puncture extending through a tissue having an introducer sheath therein, comprising
- a cartridge comprising a proximal end, a distal end sized for insertion through the introducer sheath within the puncture extending through the tissue, and a lumen extending between the proximal end and the distal end of the cartridge;
- a locking element carried on the cartridge and sized for introduction into a lumen of the introducer sheath and comprising one or more first detents for engaging the proximal end of the introducer sheath when the cartridge is inserted into the introducer sheath such that a subsequent proximal movement of the cartridge causes a corresponding proximal movement of the introducer sheath, wherein the cartridge is coupled to at least one second detent, and wherein the locking element comprises a sleeve with a passage therethrough configured to receive the at least one second detent to thereby couple the cartridge to the locking element;
- a sealant disposed within the lumen of the cartridge; and
- a pusher member disposed within the lumen of the cartridge for deploying the sealant distally from the lumen of the cartridge when the cartridge is retracted proximally relative to the pusher member.

10. The apparatus of claim 9, wherein the first one or more detents are compressible radially inwardly to accommodate insertion into the lumen of the introducer sheath and resiliently expandable to an enlarged condition to engage one or more mating features within the introducer sheath.

11. The apparatus of claim 10, wherein the sleeve comprises an extension sized for introduction into the lumen proximal end of the introducer sheath, the extension carrying the first one or more detents.

* * * * *